United States Patent
Tat et al.

(10) Patent No.: US 10,557,787 B1
(45) Date of Patent: Feb. 11, 2020

(54) DETECTION OF COMPOUNDS IN MATERIAL SAMPLES UTILIZING A TRANSFORMATION AND SUBSEQUENT DECOMPOSITION

(71) Applicant: The Boeing Company, Chicago, IL (US)

(72) Inventors: Hong Hue Tat, Redmond, WA (US); Yuan-Jye Wu, Issaquah, WA (US); David K. Mefford, Brownsboro, AL (US); Robert Alan Smith, Hampton Cove, AL (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 16/186,386

(22) Filed: Nov. 9, 2018

(51) Int. Cl.
  *G01N 21/00* (2006.01)
  *G01N 21/31* (2006.01)
  *G01N 21/35* (2014.01)

(52) U.S. Cl.
  CPC ......... *G01N 21/3103* (2013.01); *G01N 21/35* (2013.01); *G01N 2201/126* (2013.01)

(58) Field of Classification Search
  CPC .............. G01N 21/3103; G01N 21/35; G01N 2201/126
  See application file for complete search history.

(56) References Cited

U.S. PATENT DOCUMENTS

| | | | |
|---|---|---|---|
| 7,219,020 B1 * | 5/2007 | Hull ...................... | G16C 20/40 702/27 |
| 2004/0111220 A1 * | 6/2004 | Ochs ........................ | G01S 3/16 702/19 |
| 2015/0206060 A1 * | 7/2015 | Coles ..................... | G06N 7/005 706/12 |

* cited by examiner

*Primary Examiner* — David P Porta
*Assistant Examiner* — Mamadou Faye
(74) *Attorney, Agent, or Firm* — Yee & Associates, P.C.

(57) ABSTRACT

A method of detecting a compound in a material sample is presented. A transformation is generated from a set of IR spectra of a set of identified compounds, in which the compound is one of the set of identified compounds. The transformation is applied to an IR spectrum of the material sample to form a transformed IR spectrum. A decomposition is applied to the transformation. Results indicative of a presence or an absence of the compound are generated based on an output of the decomposition.

21 Claims, 12 Drawing Sheets

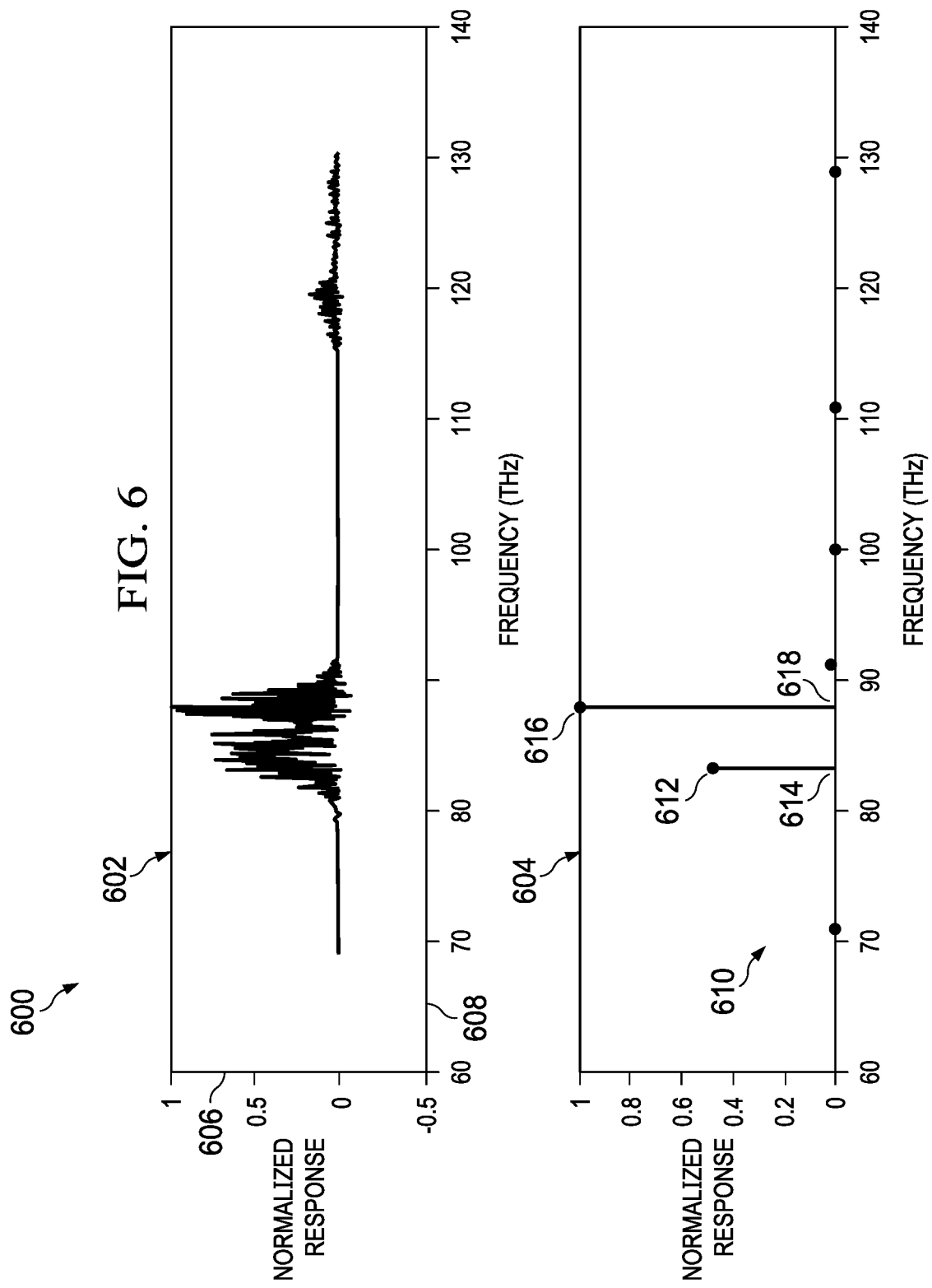

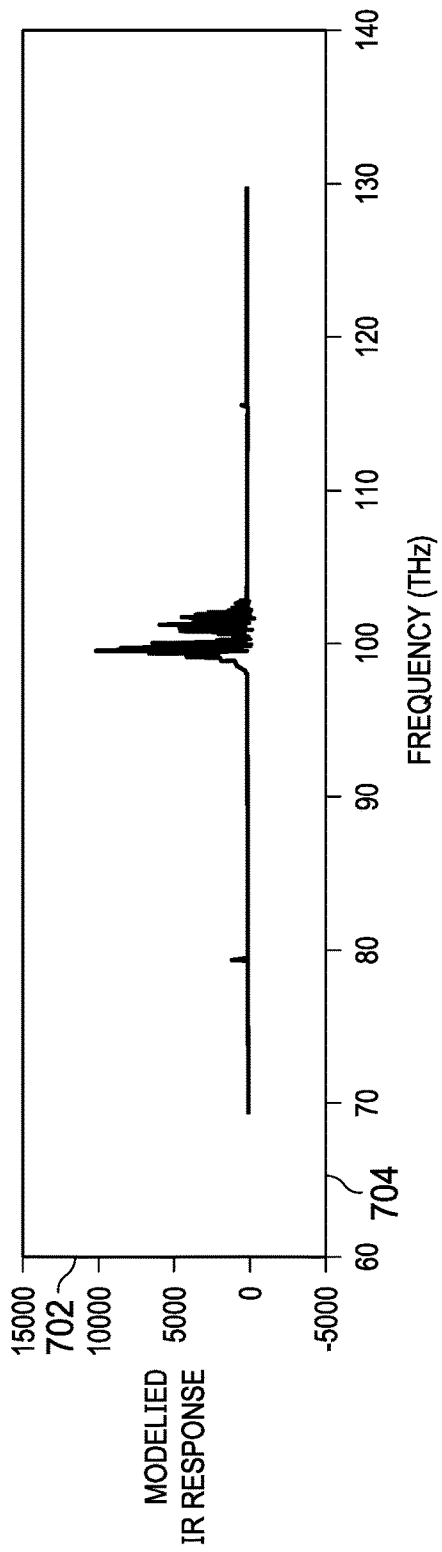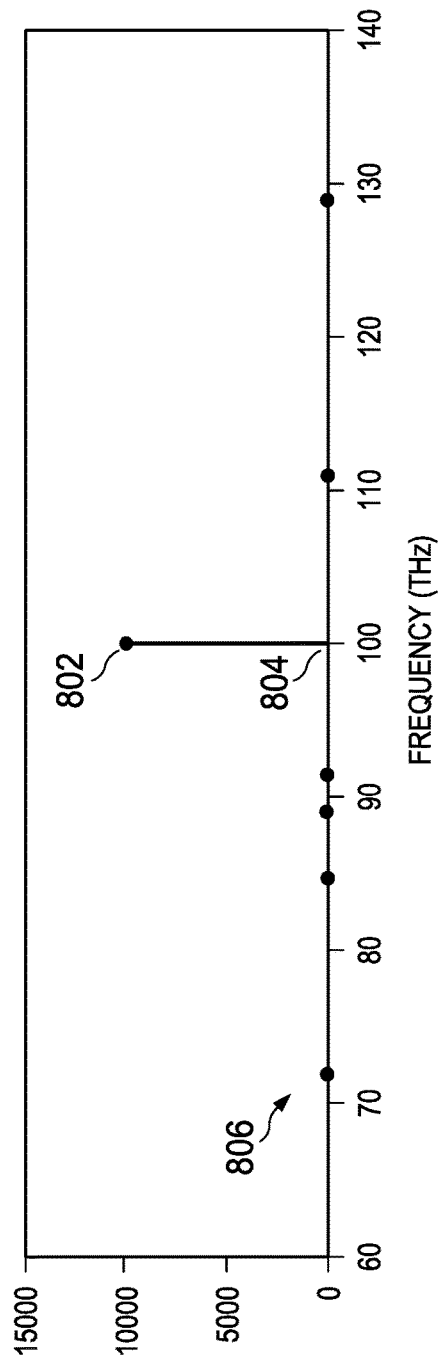

DETECTION OF COMPOUNDS IN MATERIAL SAMPLES UTILIZING A TRANSFORMATION AND SUBSEQUENT DECOMPOSITION

BACKGROUND INFORMATION

1. Field

The present disclosure relates generally to compound detection, and more specifically, to detecting compounds using infrared (IR) spectroscopy. Yet more specifically, the present disclosure relates to processing of an IR spectrum using a transformation and subsequent decomposition for detection of a set of compounds in a material sample.

2. Background

Infrared spectroscopy involves interrogating an area or sample with infrared energy. The chemical bonds of the compounds present will interact with the infrared energy and produce a spectral response that can be measured.

It is often undesirably difficult to determine the presence or absence of substances in a sample. It is particularly difficult to detect specific chemicals when compounds are mixed or there are unknown substances due to environment (clutter signals). The more complex the composition of a sample, the more difficult it becomes to determine which peaks in the IR spectrum are from which functional group. Further, hundreds of known functional groups absorb in the mid-IR range and may result in thousands of peaks increasing the difficulty of determining what peaks are from what functional groups.

Therefore, it would be desirable to have a method and apparatus that take into account at least some of the issues discussed above, as well as other possible issues. For example, it would be desirable to have a method and apparatus to determine the presence of chemical or biological agents based on an IR spectrum.

SUMMARY

An illustrative embodiment of the present disclosure provides a method of detecting a compound in a material sample. A transformation is generated from a set of IR spectra of a set of identified compounds, in which the compound is one of the set of identified compounds. A transformation is applied to an IR spectrum of the material sample to form a transformed IR spectrum. A decomposition is applied to the transformed IR spectrum. Results indicative of a presence or an absence of the compound are generated based on an output of the decomposition.

Another illustrative embodiment of the present disclosure provides a method of monitoring samples for presence of a set of identified compounds. A set of identified frequencies for the set of identified compounds is determined. A transformation is applied to an IR spectrum of a material sample to form a reduced IR spectrum having only the set of identified frequencies. A compressed sensing decomposition is performed on the reduced IR spectrum.

Yet another illustrative embodiment of the present disclosure provides an apparatus for monitoring for a set of identified compounds in material samples. The apparatus comprises a chemical analyzer configured to apply a transformation to an IR spectrum of a material sample to form a transformed IR spectrum, apply a decomposition to the transformed IR spectrum, and generate results based on an output of the decomposition.

A yet further illustrative embodiment of the present disclosure provides a computer program product for detecting a compound in a material sample. The computer program product comprises a computer-readable storage medium having computer-readable program code embodied therewith. The computer-readable program code is executable by one or more computer processors to generate a transformation from a set of IR spectra of a set of identified compounds, in which the compound is one of the set of identified compounds, apply a transformation to an IR spectrum of the material sample to form a transformed IR spectrum; apply a decomposition to the transformed IR spectrum; and generate results indicative of a presence or an absence of the compound based on an output of the decomposition.

Another illustrative embodiment of the present disclosure provides a method for monitoring for a set of identified compounds in a material sample. A set of identified frequencies is received at an IR spectrometer, wherein the set of identified frequencies is selected for the set of identified compounds. The material sample is loaded into the IR spectrometer. A reduced IR spectrum for the material sample is generated using the IR spectrometer, wherein the reduced IR spectrum has only the set of identified frequencies.

A further illustrative embodiment of the present disclosure provides a method for monitoring for a set of identified compounds in a material sample. A transformation is received at an IR spectrometer, wherein the transformation is a matrix generated for the detection of the set of identified compounds. The material sample is loaded into the IR spectrometer. A transformed IR spectrum for the material sample is generated using the IR spectrometer by sampling only frequencies used in the transformation.

A further illustrative embodiment of the present disclosure provides a method for monitoring for a set of identified compounds in a material sample. A transformation is received at an IR spectrometer, wherein the transformation is a matrix generated for the detection of the set of identified compounds. The material sample is loaded into the IR spectrometer. A transformed IR spectrum is generated for the material sample using the IR spectrometer by sampling only frequencies used in the transformation.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

FIG. 6 is an illustration of a normalized IR spectrum and a reduced IR spectrum for a third compound in accordance with an illustrative embodiment;

FIG. 7 is an illustration of an IR spectrum for a material sample in accordance with an illustrative embodiment;

FIG. 8 is an illustration of a reduced IR spectrum for a material sample in accordance with an illustrative embodiment;

DETAILED DESCRIPTION

The illustrative embodiments recognize and take into account one or more different considerations. For example, the illustrative embodiments recognize and take into account that existing methods of analyzing an IR spectrum consist of comparing a measured signal to a library of known signals. The library of known signals includes known compounds that may be present in the material sample. A comparison can be done via statistical correlation methods or machine learning. The illustrative embodiments recognize and take into account that comparing a measured signal to a library of known signals may be undesirable.

The illustrative embodiments recognize and take into account that these methods of comparing a measured signal to a library of known signals do not work well when there is a signal due to a mixture of compounds or there are unknown compounds. For instance, to measure even the presence of three compounds, a machine learning method would need to know all the possible combinations of the three compounds. It would be undesirably time-consuming and costly to determine all possible combinations. The number of combinations grows exponentially for more compounds. The illustrative embodiments recognize and take into account that the likelihood of successfully identifying the mixed compounds decreases with the increased quantity of compounds.

The illustrative embodiments recognize and take into account that spectral decomposition with a linear least squares fit may be used to analyze an IR spectrum. However, the illustrative embodiments also recognize and take into account that the least squares solution can lead to the computed solution having many non-zero (or non-negligible) entries which is not realistic. There can't be a negative amount for a substance. Additionally, the illustrative embodiments recognize and take into account that decomposition alone does not have a good solution for handling unknown signatures.

The illustrative embodiments provide an apparatus and methods to process a measured IR spectrum to determine the presence of chemical/biological agents based on the spectral response. The illustrative embodiments recognize that it would be desirable to provide methods for analyzing a spectral response to determine what chemical compounds or chemical functional groups are present.

Figure 1:
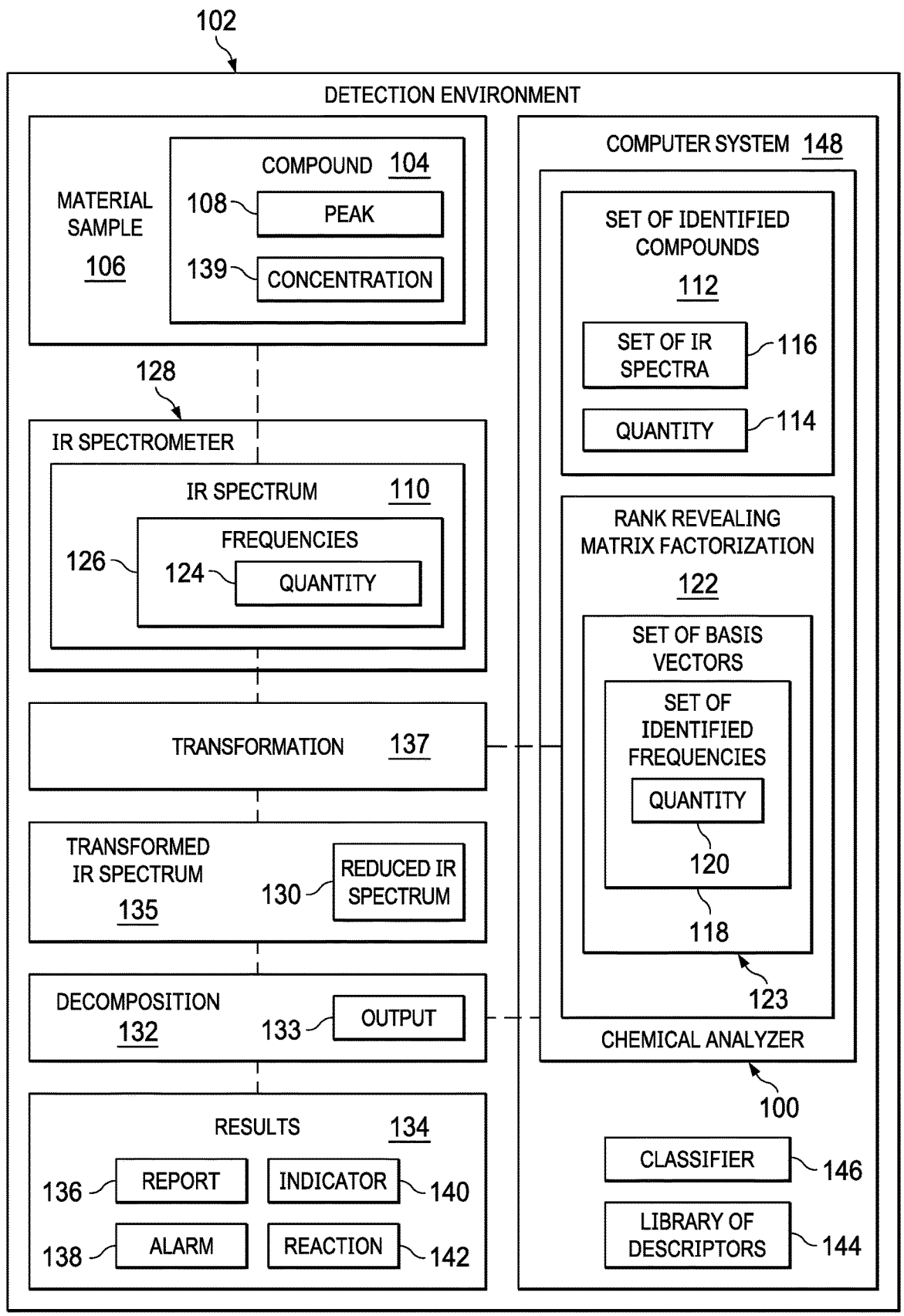
FIG. 1 is an illustration of a block diagram of a detection environment in which a chemical analyzer operates in accordance with an illustrative example.

Turning now to FIG. 1, an illustration of a block diagram of a detection environment in which a chemical analyzer operates is depicted in accordance with an illustrative embodiment. Chemical analyzer 100 in detection environment 102 is configured to detect compound 104 in material sample 106. For example, chemical analyzer 100 is configured to detect compound 104 having peak 108 that would otherwise be obscured in IR spectrum 110 of material sample 106.

Chemical analyzer 100 is able to detect levels compound 104 previously undetectable by conventional detection mechanisms. Chemical analyzer 100 reduces time to analyze material sample 106.

Chemical analyzer 100 is provided set of identified compounds 112. As used herein, a "set" includes one or more items. For example, set of identified compounds 112 includes one or more identified compounds. Set of identified compounds 112 has any desirable quantity 114 of identified compounds.

Set of identified compounds 112 includes any desirable chemical, pharmaceutical, or biological compounds for detection. Set of identified compounds 112 is selected through any desirable process. Set of identified compounds 112 is selected for a specific function or specific application. For example, when detection environment 102 includes a portable heater, set of identified compounds 112 may be selected for detection of potentially hazardous byproducts, such as carbon monoxide. As another example, when detection environment 102 includes a security area, set of identified compounds 112 may include explosive materials or other undesirable materials for a security area.

Set of identified compounds 112 has set of IR spectra 116. Set of IR spectra 116 includes respective infrared (IR) spectra for each identified compound of set of identified compounds 112. Set of IR spectra 116 receives preprocessing including removal of sensor transfer function if known. The preprocessing of set of IR spectra 116 includes normalizing each IR spectrum of set of IR spectra 116 to a same y-axis. In some illustrative examples, frequency distribution functions are optionally calculated from set of IR spectra 116.

When used, frequency distribution functions provide a compression mechanism. When used, frequency distribution functions also provide a mechanism to handle sensor noise or variation. By using a frequency spacing that is tailored to a measured variance would produce an improved representation of the chemical signature.

After preprocessing, rank revealing matrix factorization 122 is applied to a matrix formed by set of IR spectra 116 of set of identified compounds 112. The rank revealing factorization method generates set of basis vectors 123 for set of identified compounds 112 and transformation 137. The rank revealing factorization method takes any desirable form.

Set of basis vectors 123 includes a basis vector for each compound of set of identified compounds 112. Set of basis vectors 123 is used to distinguish each of set of identified compounds 112 from other compounds. The basis vector for a compound has a same quantity of entries as each other basis vector in set of basis vectors 123. Basis vectors include a quantity of labels and a value assigned to each label.

Transformation 137 is configured to create a transformed IR spectrum having a same quantity of entries as each of the basis vectors of set of basis vectors 123. Transformation 137 is configured to create a transformed IR spectrum having equal to or greater than a quantity of compounds in a set of identified compounds.

Entries for each of the basis vectors are calculated from set of IR spectra 116. In some illustrative examples, each basis vector in set of basis vectors 123 is a reduced IR spectrum comprising set of identified frequencies 118 for each compound of set of identified compounds 112. When a basis vector contains respective values for set of identified frequencies 118, the quantity of labels is the quantity of frequencies in set of identified frequencies 118, each label is a respective frequency of set of identified frequencies 118, and each value is a respective value of the respective frequency. In some illustrative examples, when set of basis vectors 123 contains respective values for set of identified frequencies 118, a "rank revealing" QR or LU factorization method is employed. Column pivoting is one of many rank-revealing algorithms. Sometimes column pivoting may also be referred to as a spectrum-revealing method. In some illustrative examples, set of identified frequencies 118 is calculated using QR factorization with column pivoting from a matrix formed by set of IR spectra 116 of set of identified compounds 112.

Quantity 120 of frequencies in set of identified frequencies 118 is equal to or greater than quantity 114 of identified compounds in set of identified compounds 112. Quantity 120 and locations of frequencies of set of identified frequencies 118 is determined using set of IR spectra 116.

Set of identified frequencies 118 includes frequencies to identify each of set of identified compounds 112. Respective values for each of set of identified frequencies 118 are used to distinguish a compound from each other compound of set of identified compounds 112.

Quantity 120 is significantly less than a quantity of frequencies in set of IR spectra 116. For example, an IR spectrum of set of IR spectra 116 may have thousands of frequencies, or samples. By generating set of basis vectors 123, the dataset for set of identified compounds 112 is greatly reduced. For example, a matrix including set of IR spectra 116 has thousands of rows corresponding to each frequency of set of IR spectra 116, while a basis vector of the set of basis vectors has a quantity of entries possibly as low as the quantity of compounds in set of identified compounds 112. By performing rank revealing matrix factorization 122, analysis of a material sample for set of identified compounds 112 has at least one of a reduced time or reduced computational resources.

In other illustrative examples, set of basis vectors 123 is a vector with a mixed spectrum basis. In these illustrative examples, a truncated SVD (Singular Value Decomposition) or rank-revealing URV/ULV is used. When a basis vector includes a mixed spectrum basis, at least one label is a formula that may contain more than one frequency of set of IR spectra 116, and a respective value for that label is a calculated value by applying the formula to the respective values of the more than one frequency. The reduced space formed by a set of basis vectors of a mixed spectrum basis contains more characteristics of identified compounds since each basis vector contains multiple spectra information.

Rank revealing matrix factorization 122 calculates transformation 137. In some illustrative examples, transformation 137 is a matrix configured to create a vector having a same quantity of entries as each basis vector of set of basis vectors 123 when applied to an IR spectrum of a material sample, such as IR spectrum 110 of material sample 106.

After calculating transformation 137, transformation 137 is applied to IR spectrum 110 to calculate transformed IR spectrum 135. Transformed IR spectrum 135 is a vector having the same quantity of entries as the quantity of entries of each of set of basis vectors 123.

In some illustrative examples, transformed IR spectrum 135 takes the form of reduced IR spectrum 130. When transformed IR spectrum 135 takes the form of reduced IR spectrum 130, the respective values for each of set of identified frequencies 118 for material sample 106 are present in transformed IR spectrum 135. In these illustrative examples, a subset of IR spectrum 110 of material sample 106 is used to achieve dimensional reduction. In these illustrative examples, set of identified frequencies 118 are selected from IR spectrum 110. In these illustrative examples, transformed IR spectrum 135 for material sample 106 is the same as the respective values for set of identified frequencies 118 for material sample 106.

Quantity 120 of frequencies in set of identified frequencies 118 is significantly less than quantity 124 of frequencies 126 of IR spectrum 110 of material sample 106. IR spectrum 110 is provided by IR spectrometer 128 and has several thousands of points of data. When transformation 137 is applied to IR spectrum 110, transformed IR spectrum 135 is created. Transformed IR spectrum 135 takes the form of a vector having a quantity of entries substantially less than quantity 124 of frequencies 126 in IR spectrum 110. In some illustrative examples, transformed IR spectrum 135 takes the form of reduced IR spectrum 130. Reduced IR spectrum 130 only includes frequencies from set of identified frequencies 118.

In some illustrative examples, IR spectrometer 128 receives set of identified frequencies 118 prior to IR spectrometer 128 generating a spectrum for material sample 106. In these illustrative examples, rather than IR spectrometer 128 generating IR spectrum 110, IR spectrometer 128 instead generates reduced IR spectrum 130. When IR spectrometer 128 generates reduced IR spectrum 130, a processing time for material sample 106 in IR spectrometer 128 is reduced. Generating IR spectrum 110 using IR spectrometer 128 takes a longer amount of time than generating reduced IR spectrum 130 using IR spectrometer 128.

In some other illustrative examples, transformed IR spectrum 135 for material sample 106 is calculated using IR spectrum 110 to form a mixed spectrum. In these illustrative examples, transformed IR spectrum 135 for material sample 106 is not identical to a reduced IR spectrum for material sample 106. In these illustrative examples, transformed IR spectrum 135 comprises calculated values achieved by applying a respective formula from a respective label to a respective number of values in IR spectrum 110 of material sample 106. For example, an entry in transformed IR spectrum 135 may combine the product of a value at a first frequency and a first constant with the product of a value at a second frequency and a second constant to form a calculated value for the entry, where the formula is the respective label of the entry and the calculated value is the respective value of the entry.

Applying transformation 137 serves as a compression mechanism for IR spectrum 110. Compression aids in reducing the computational resources utilized during the decomposition step and also reduces data transmission needs for IR spectrum 110.

Chemical analyzer 100 performs decomposition 132 on transformed IR spectrum 135. More specifically, in some illustrative examples, chemical analyzer 100 performs compressed sensing decomposition. Decomposition 132 determines the presence or absence of each of set of identified compounds 112. Decomposition 132 also determines a concentration of each of set of identified compounds 112.

Decomposition 132 produces output 133. Output is a series of numerical values. Output 133 is a numerical value for each compound in set of identified compounds 112.

In some illustrative examples, it is determined whether decomposition 132 was successful. Decomposition 132 is not successful when negative values are returned. In some illustrative examples, if decomposition 132 is successful, results 134 are generated in response.

Results 134 are generated based on output 133 of decomposition 132. Results 134 are indicative of a presence or an absence of a compound, such as compound 104. More specifically, results 134 are indicative of a presence or an absence of each compound of set of identified compounds 112. In some illustrative examples, results 134 are indicative of the presence of one or more compounds of set of identified compounds 112.

Results 134 take any desirable form. In some illustrative examples, results 134 take the form of report 136. In some illustrative examples, report 136 includes a listing of any of set of identified compounds 112 present in material sample 106. In some illustrative examples, report 136 includes a concentration of any of set of identified compounds 112 present in material sample 106.

In one example, report 136 includes compound 104. As another example, report 136 includes concentration 139 of compound 104 within material sample 106. Concentration 139 is determined using decomposition 132.

In some illustrative examples, results 134 take the form of alarm 138. Alarm 138 takes the form of any desirable type of alarm, including an audible alarm or a visual alarm. Alarm 138 can be a siren, an announcement, a beeping, or any other desirable type of audible alarm. In some illustrative examples, alarm 138 is triggered when concentration 139 is above a desired limit. In some illustrative examples, alarm 138 is triggered when compound 104 is present.

In some illustrative examples, results 134 take the form of indicator 140. Indicator 140 takes any desirable form such as text, an icon, a light, a flag, a switch, a color, or any other desirable type of indicator. In some illustrative examples, indicator 140 is activated when compound 104 is present. In some illustrative examples, indicator 140 is indicative of concentration 139 of compound 104.

In some illustrative examples, results 134 take the form of reaction 142. Reaction 142 takes the form of a physical change within detection environment 102. Reaction 142 takes any desirable form. In some illustrative examples, when material sample 106 is an air sample, reaction 142 is a change to air flow within detection environment 102. In some illustrative examples, reaction 142 includes at least one of venting air from detection environment 102, increasing exterior air brought into detection environment, increasing filtration of air within detection environment 102, or increasing or decreasing circulation of air within detection environment 102.

In some illustrative examples, reaction 142 includes beginning a fire suppression system. In some illustrative examples, reaction 142 includes disposing of material sample 106. In some illustrative examples, reaction 142 includes marking a product for disposal. In some illustrative examples, reaction 142 includes stopping a production line or placing a machine down for maintenance.

In some illustrative examples, decomposition 132 is unsuccessful. When decomposition 132 is unsuccessful, output 133 may include negative values. In some illustrative examples, when decomposition 132 is unsuccessful, an alert is generated that decomposition 132 was unsuccessful. In some illustrative examples, when decomposition 132 is unsuccessful, a different method of analysis may be optionally applied to IR spectrum 110.

If any of the values in output 133 of decomposition 132 are negative, additional analysis of material sample 106 is performed. In some illustrative examples, the additional analysis is performed on IR spectrum 110 of material sample 106. In some illustrative examples, the additional analysis is performed on a remainder of IR spectrum 110 without reduced IR spectrum 130. In other illustrative examples, the additional analysis is performed on reduced IR spectrum 130. The analysis is performed on one of IR spectrum 110, reduced IR spectrum 130, or the remainder spectrum to determine which of the set of identified compounds 112 is the closest match using machine learning. In some illustrative examples, to perform the machine learning, the threshold for determination of a compound may be set lower during this analysis. The machine learning returns the closest match compound of set of identified compounds 112 and the difference in spectra between the closest compound and the one of IR spectrum 110, reduced IR spectrum 130, or the remainder spectrum receiving he additional analysis.

Library of descriptors 144 may be generated based on an analysis of IR spectra for known compounds. For example, library of descriptors 144 may include set of IR spectra 116 for set of identified compounds 112. Library of descriptors 144 may include entire spectra or a portion of the spectra of materials, such as identifying peaks of materials.

Library of descriptors 144 is used to train classifier 146. Classifier 146 is configured to determine a type of chemical within material sample 106. Classifier 146 takes a longer period of time to identify a chemical within material sample 106 than chemical analyzer 100.

Chemical analyzer 100 enables separation of signatures of compound 104 from background signals in material sample 106 by creation of transformed IR spectrum 135 and performing decomposition 132 on transformed IR spectrum 135. Chemical analyzer 100 provides detection of compound 104 in material sample 106 when conventional detection mechanisms fail to detect compound 104.

Chemical analyzer 100 enables detection of several compounds simultaneously. Further, chemical analyzer 100 detects compounds of set of identified compounds 112 without a classification step for a first known substance.

Although chemical analyzer 100 is described as detecting compound 104 in material sample 106, chemical analyzer may be used to detect any desirable level of granularity. For example, in some illustrative examples, chemical analyzer 100 could be used to detect a specific type of bonds or a specific quantity of bonds.

Additionally, the analysis performed by chemical analyzer 100 would be beneficial for training systems through machine learning. For example, a transformation and decomposition of the illustrative examples may be performed to create library of descriptors 144 used to train classifier 146.

The illustration of detection environment 102 and chemical analyzer 100 in FIG. 1 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, although computer system 148 is depicted in detection environment 102 with IR spectrometer 128, in some illustrative examples computer system 148 and IR spectrometer 128 may be physically separated. For example, computer system 148 may be in a different room, a different building, or even a different geographical region than IR spectrometer 128. Additionally, any desirable connection exists between IR spectrometer 128 and computer system 148. In some illustrative examples, IR spectrometer 128 and computer system 148 communicate via wireless communication. In some other illustrative examples, IR spectrometer 128 and computer system 148 communicate via wired communication.

Further, although only one material sample, material sample 106, is depicted, chemical analyzer 100 can be used repeatedly for a plurality of samples. Chemical analyzer 100 is used to detect compounds in any desirable quantity of compounds. Additionally, chemical analyzer 100 may be used to analyze IR spectra generated by several different IR spectrometers.

Figure 2:
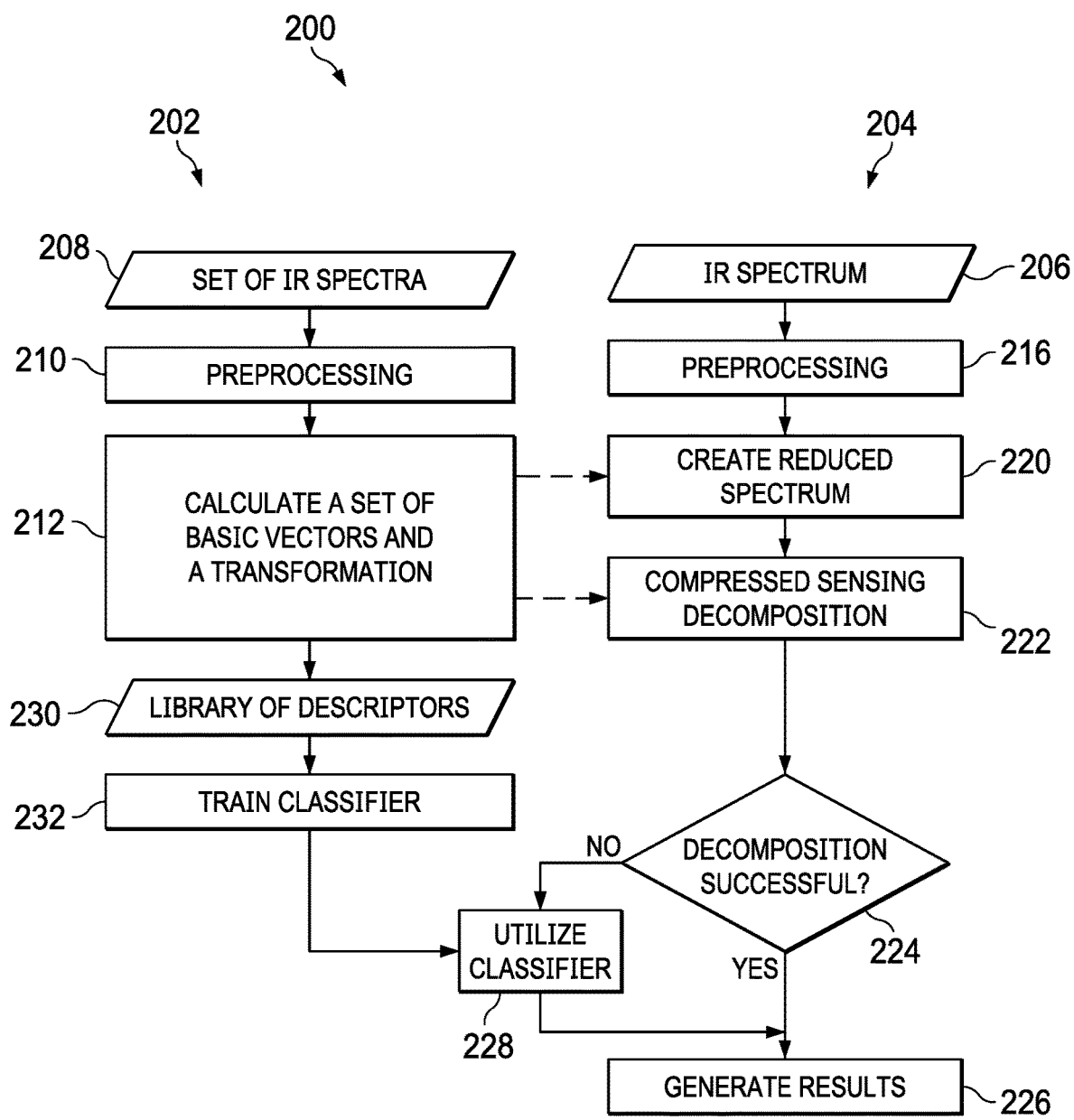
FIG. 2 is an illustration of a flowchart in accordance with an illustrative embodiment.

Turning now to FIG. 2, an illustration of a flowchart is depicted in accordance with an illustrative embodiment. Flowchart 200 includes process 202 and process 204. In process 204, IR spectrum 206 is analyzed to detect a compound in a material sample. Process 202 supports process 204.

In process 202, set of IR spectra 208 of a set of identified compounds is received. Set of IR spectra 208 is an example of set of IR spectra 116 of FIG. 1. At operation 210, set of IR spectra 116 receives preprocessing. Preprocessing includes any desirable types of processing to improve spectral quality, including preprocessing to reduce scatter, reduce background, or remove the sensor transfer function if known. Preprocessing in operation 210 takes any desirable form, including but not limited to high or low pass frequency filtering, averaging, or deconvolution. When deconvolution is present, deconvolution is used to remove the sensor transfer function.

Optionally, frequency distribution functions may be calculated for set of IR spectra 208. When frequency distribution functions are calculated, the frequency distribution functions provide compression and compensate for sensor noise or variation.

To form frequency distribution functions, frequency bins are calculated from 0 to the maximum frequency with a spacing of $\Delta f$. Calculating the frequency bins creates the horizontal axis of the histogram.

When frequency distribution functions are calculated, after calculating the frequency bins, top $N_f$ frequencies are identified for each spectrum and the correlating frequency bins are identified. The value in each of the identified frequency bins is increased by either a count of the peak or the amplitude of the peak.

After preprocessing at operation 210, a set of basis vectors and a transformation are calculated at operation 212. The set of basis vectors is calculated using the set of IR spectra having received preprocessing in operation 210. The set of basis vectors is an implementation of set of basis vectors 123 in FIG. 1.

In some illustrative examples, the set of basis vectors and the transformation are calculated using rank revealing matrix factorizations. In some illustrative examples, the set of basis vectors and the transformation are calculated using QR factorization with column pivoting from a matrix formed by set of IR spectra of set of identified compounds.

There are n compounds with m frequencies in each spectrum of the set of IR spectra. The n compounds with m frequencies are used to form a matrix A that is m×n where the set of IR spectra for the set of identified compounds are the rows of A. The $A_{mn}$ element is the amplitude of the mth frequency for compound n.

A rank revealing matrix factorization is performed on the transpose of the matrix A. An orthogonal-triangular decomposition of matrix $A^T$ where A is m by n, produces a n×m upper triangular matrix R and an n×n unitary matrix Q so that $A^T=Q*R$ and a permutation matrix E so that $A^T*E=Q*R$. E is calculated such that the magnitude of the diagonal elements of R are decreasing. The set of identified frequencies for the transformation to produce a reduced IR spectrum are selected based on the first n diagonal entries of the matrix E.

The rank revealing matrix factorization is an implementation of rank revealing matrix factorization 122 of FIG. 1. Rank revealing matrix factorization creates a set of basis vectors and a transformation. In some illustrative examples, rank revealing matrix factorization is a reduction to be applied to an IR spectrum to select the set of identified frequencies in the IR spectrum.

In process 204, the transformation calculated at operation 212 is used to perform an analysis on IR spectrum 206. IR spectrum 206 is analyzed to detect a compound in a material sample.

Preprocessing is performed on IR spectrum 206 at operation 216. Preprocessing in operation 216 is the same preprocessing performed on the set of IR spectra 208 in operation 210.

Optionally, frequency distribution functions are calculated for IR spectrum 206. When frequency distribution functions are calculated for set of IR spectra 208, frequency distribution functions are calculated for IR spectrum 206. When frequency distribution functions are not calculated for set of IR spectra 208, frequency distribution functions are not calculated for IR spectrum 206. The properties applied to calculate frequency distribution functions for set of IR spectra 208 are applied in calculating frequency distribution functions for IR spectrum 206.

After preprocessing 216 and optionally calculating frequency distribution functions, the transformation calculated in operation 212 is applied to IR spectrum 206. Applying the transformation creates transformed IR spectrum in operation 220.

A compressed sensing decomposition is performed on the transformed IR spectrum during operation 222. The compressed sensing decomposition produces an output. The output is used to produce results. In some illustrative examples, the results are indicative of one of an absence or a presence of one or more compounds of set of identified compounds.

A decomposition is described by the equation:

$$F(v) = \sum_{i=1}^{n} \beta_i f_i(v) + g(v) + \text{noise}$$

Equation 1. Linear model of observed spectrum

The measured spectrum (F(v)) which has m frequency components is assumed to be a linear combination of the spectral responses for n known individual substances, $f_i = [f_{i1}, \ldots, f_{im}]^T$ weighted by value $\beta = [\beta_1, \ldots, \beta_n]T$, g(v) which are responses from unknown substances, and noise. The scaling terms $\beta_i$ is a parameter that correlates the change in amplitude of the IR spectrum to the concentration of the agent.

A least squares approach seeks a vector $\beta = [\beta_1, \ldots, \beta_n]^T$ to minimize the error in L2 norm $$\left( \min_{x_i} \sum_{j=1}^{m} \left( F_j - \sum_{i=1}^{n} \beta_i f_{ij} \right)^2 \right)$$

between the measured and calculated spectra. However, the least squares solution can lead to the vector $\beta$ having many non-zero (or non-negligible) entries which is not realistic. There can't be a negative amount for a substance.

Another approach is a compressed sensing approach which seeks to find a sparse solution for $\beta$. The assumption is that not all possible chemicals of interest will be present simultaneously, so $\beta$ should be predominantly zero with a few non-zero values corresponding to the agents that are present. One sparse vector approach is to minimize the L1 norm $$\left( \min_{x_i} \sum_{j=1}^{m} \left\| F_j - \sum_{i=1}^{n} \beta_i f_{ij} \right\|_1 \right).$$

In some illustrative examples, after performing compressed sensing decomposition 222, it is determined if the decomposition was successful at operation 224. If the decomposition is successful at operation 224, results are generated at operation 226 using the output of compressed sensing decomposition 222. Results may be results 134 of FIG. 1.

If the decomposition is not successful at operation 224, an alert may optionally be provided. For example, an alert may be provided to an operator that the decomposition was unsuccessful. An alert may provide an opportunity for the operator to provide additional investigation.

If the decomposition is not successful at operation 224, process 204 may optionally utilize a classifier on IR spectrum 206 at operation 228. In some illustrative examples, classifier used at operation 228 produces results at operation 226.

The classifier utilized in operation 228 is created by process 202. For example, library of descriptors 230 is generated using set of IR spectra 208. In operation 232, a classifier is trained using the library of descriptors.

Performing process 204 through operation 222 is significantly faster than utilizing classifier at operation 228. Further, performing process 204 through operation 222 may identify compounds at levels undetectable utilizing classifier at operation 228.

In some illustrative examples, operation 224 is optional. In these illustrative examples, results are generated at operation 226 based on the output of compressed sensing decomposition 222 in response to the output being generated.

Figure 3:
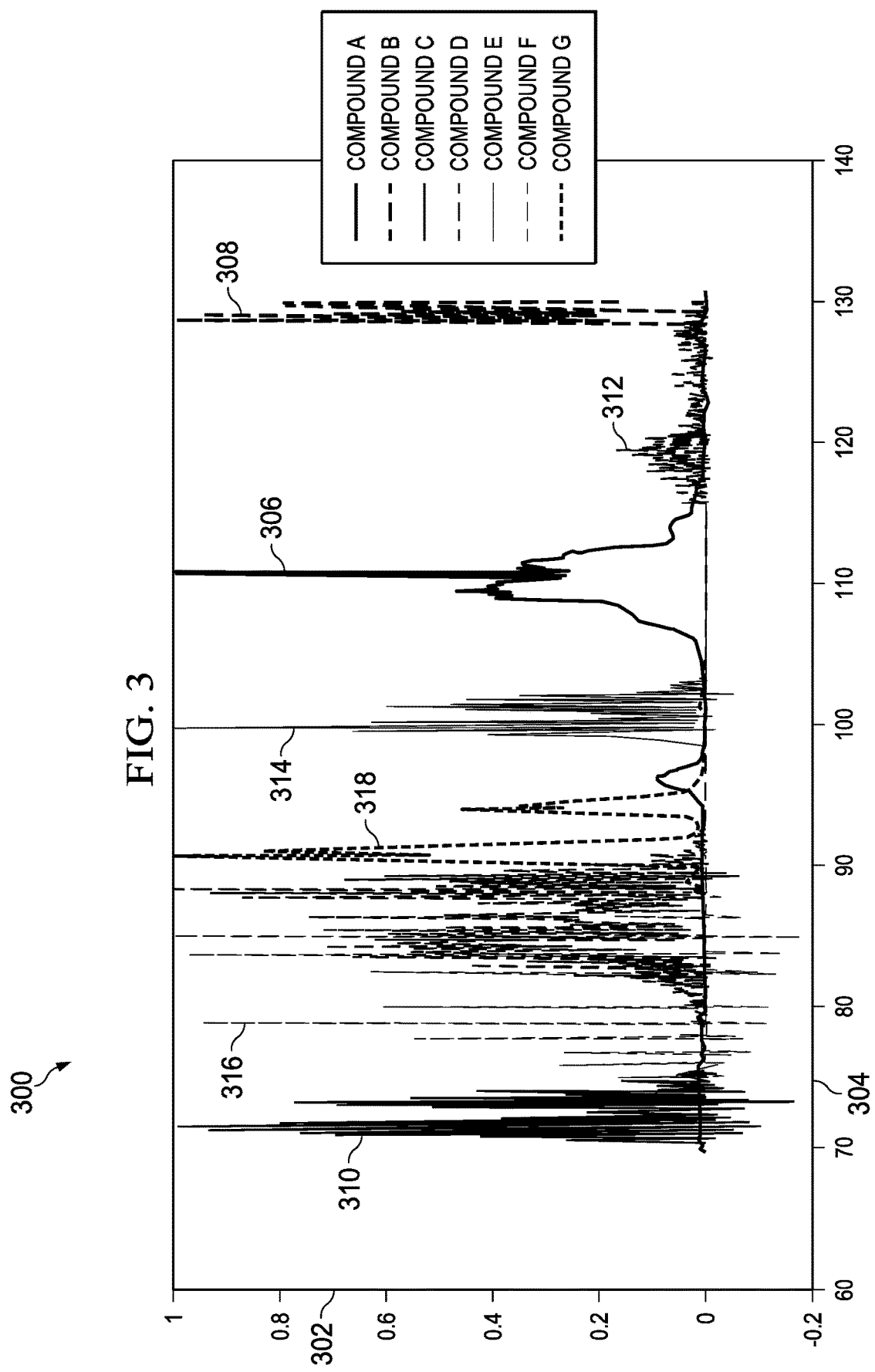
FIG. 3 is an illustration of a set of IR spectra for a set of identified compounds overlaid on each other in accordance with an illustrative embodiment.

Turning now to FIG. 3, an illustration of a set of IR spectra for a set of identified compounds overlaid on each other is depicted in accordance with an illustrative embodiment. Set of IR spectra 300 may be a physical implementation of set of IR spectra 116 of FIG. 1. Set of IR spectra 300 may be a physical implementation of set of IR spectra 208 of FIG. 2.

Set of IR spectra 300 includes a plurality of IR spectra overlaid over each other. Set of IR spectra 300 is normalized. As depicted, set of IR spectra 300 has y-axis 302 with a maximum value of 1.

Set of IR spectra 300 is displayed with x-axis 304 of frequency. Set of IR spectra 300 includes spectra for seven identified compounds. Set of IR spectra 300 includes spectrum 306 for compound A, spectrum 308 for compound B, spectrum 310 for compound C, spectrum 312 for compound D, spectrum 314 for compound E, spectrum 316 for compound F, and spectrum 318 for compound G. As can be seen in view 320, several spectra of set of IR spectra 300 overlap. For example, portions of spectrum 316 and spectrum 312 overlap. In material samples, other peaks may also be present for additional compounds. Detection of each of the identified compounds may be undesirably difficult using an IR spectrum as measured from a spectrometer.

A set of identified frequencies is calculated from set of IR spectra 300. In some illustrative examples, the set of identified frequencies is calculated using rank revealing matrix factorizations using data from set of IR spectra 300. In some illustrative examples, the set of identified frequencies is calculated using QR factorization with column pivoting from a matrix formed by set of IR spectra 300. As there are seven identified compounds, there will be at least seven frequencies in a set of identified frequencies.

Figure 4:
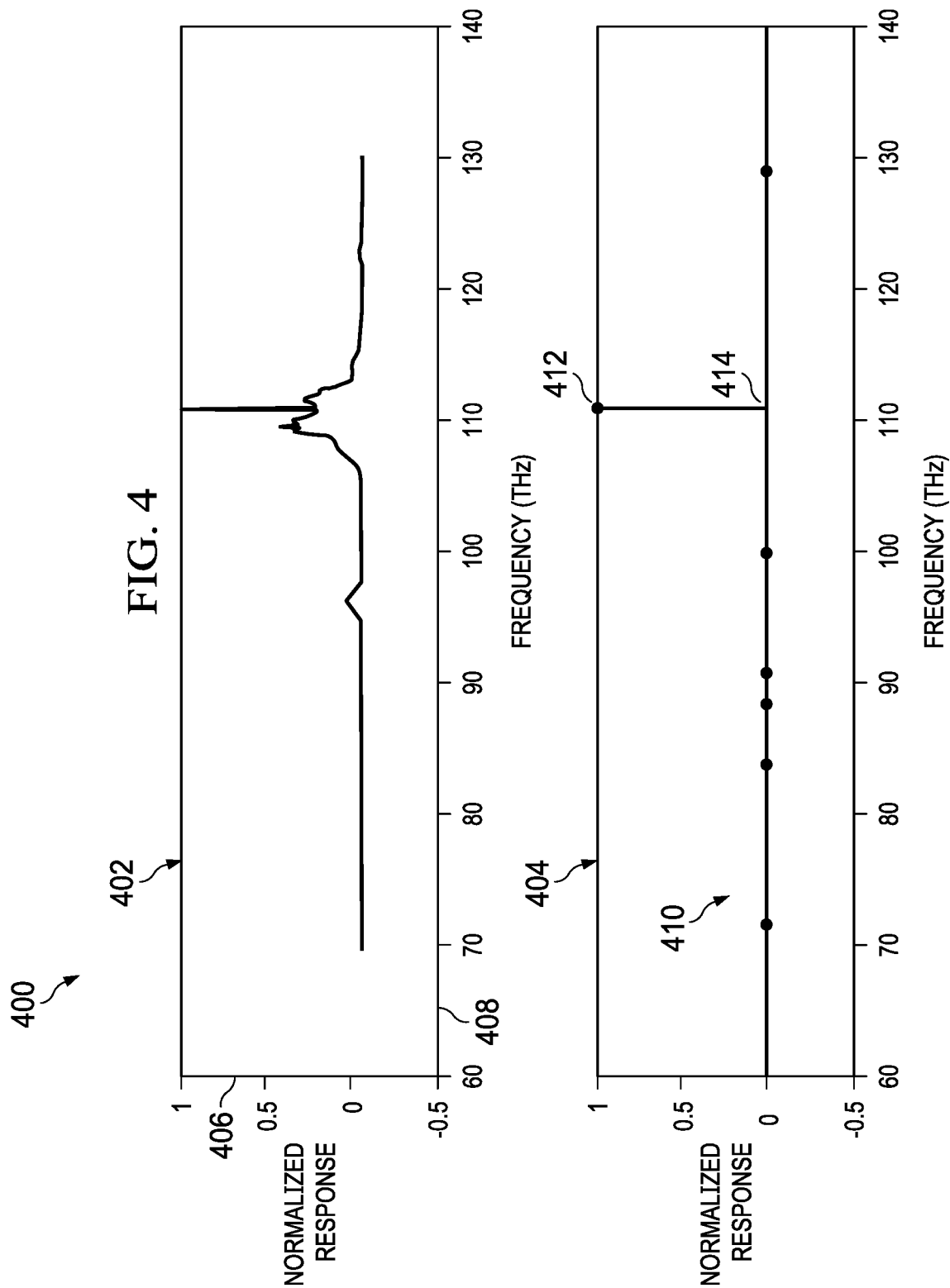
FIG. 4 is an illustration of a normalized IR spectrum and a reduced IR spectrum for a first compound in accordance with an illustrative embodiment.
Figure 5:
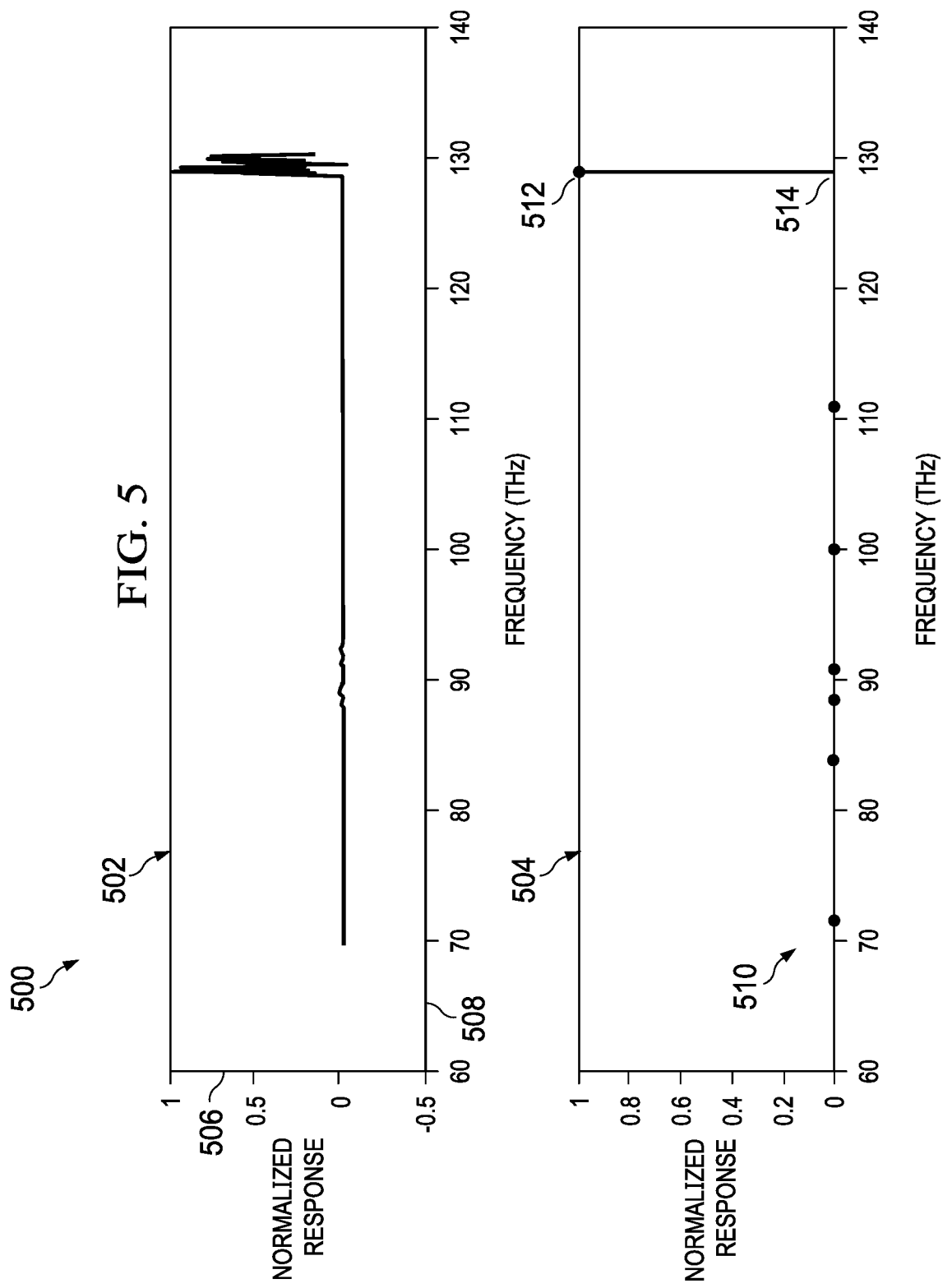
FIG. 5 is an illustration of a normalized IR spectrum and a reduced IR spectrum for a second compound in accordance with an illustrative embodiment.

FIGS. 4-6 depict an IR spectrum and associated reduced IR spectrum for different compounds of set of identified compounds in FIG. 3. Each reduced IR spectrum in FIGS. 4-6 is formed using a rank revealing matrix factorization applied to a matrix formed by set of IR spectra 300 of FIG. 3. In some illustrative examples, each reduced IR spectrum of FIGS. 4-6 is formed using a "rank revealing" QR or LU factorization method.

Turning now to FIG. 4, an illustration of a normalized IR spectrum and a reduced IR spectrum for a first compound is depicted in accordance with an illustrative embodiment. View 400 depicts IR spectrum 402 of compound A of FIG. 3 and reduced IR spectrum 404 of compound A. Each of IR spectrum 402 and reduced IR spectrum 404 has y-axis 406 of normalized response. Each of IR spectrum 402 and reduced IR spectrum 404 has x-axis 408 of frequency measured in (THz). IR spectrum 402 may be one of set of IR spectra 208 of FIG. 2.

In some illustrative examples, a rank revealing matrix factorization applied to a matrix formed by set of IR spectra 300 of FIG. 3 when applied to IR spectrum 402 forms reduced IR spectrum 404. In some illustrative examples, the rank revealing matrix factorization is a "rank revealing" QR or LU factorization method. Reduced IR spectrum 404 presents a basis vector for compound A. In the depicted illustrative example, values in the basis vector for compound A are values in reduced IR spectrum 404.

In other non-depicted examples, values in the basis vector for compound A are a mixed spectrum basis. In some of these non-depicted illustrative examples, a truncated SVD or rank-revealing URV/ULV is used.

As can be seen from view 400, applying the rank revealing matrix factorization creates reduced IR spectrum 404 with frequencies 410. Frequencies 410 has seven points.

Compound A is distinguished by a high value 412 at frequency 414 of frequencies 410 and low values for the remaining frequencies in frequencies 410. The values for each of frequencies 410 distinguish compound A from each of compound B, compound C, compound D, compound E, compound F, and compound G. In some illustrative examples, the values for each of frequencies 410 distinguish compound A from other possible compounds not included in identified compounds.

Turning now to FIG. 5, an illustration of a normalized IR spectrum and a reduced IR spectrum for a second compound is depicted in accordance with an illustrative embodiment. View 500 depicts IR spectrum 502 of compound B of FIG. 3 and reduced IR spectrum 504 of compound B. Each of IR spectrum 502 and reduced IR spectrum 504 has y-axis 506 of normalized response. Each of IR spectrum 502 and reduced IR spectrum 504 has x-axis 508 of frequency measured in (THz). IR spectrum 502 may be one of set of IR spectra 208 of FIG. 2.

In some illustrative examples, a rank revealing matrix factorization applied to a matrix formed by set of IR spectra 300 of FIG. 3 is applied to IR spectrum 502 forms reduced IR spectrum 504. In some illustrative examples, the rank revealing matrix factorization is a "rank revealing" QR or LU factorization method. Reduced IR spectrum 504 presents a basis vector for compound B. In the depicted illustrative example, values in the basis vector for compound B are values in reduced IR spectrum 504.

In other non-depicted examples, values in the basis vector for compound B are a mixed spectrum basis. In some of these non-depicted illustrative examples, a truncated SVD or rank-revealing URV/ULV is used.

As can be seen from view 500, applying the rank revealing matrix factorization creates reduced IR spectrum 504 with frequencies 510. Frequencies 510 has seven points. As can be seen in reduced IR spectrum 504, compound B is distinguished by a high value 512 at frequency 514 and low values for the remaining frequencies in frequencies 510. The values for each of frequencies 510 distinguish compound B from each of compound A, compound C, compound D, compound E, compound F, and compound G. In some illustrative examples, the values for each of frequencies 510 distinguish compound B from other possible compounds not included in identified compounds.

Turning now to FIG. 6, an illustration of a normalized IR spectrum and a reduced IR spectrum for a third compound is depicted in accordance with an illustrative embodiment. View 600 depicts IR spectrum 602 of compound D of FIG. 3 and reduced IR spectrum 604 of compound D. Each of IR spectrum 602 and reduced IR spectrum 604 has y-axis 606 of normalized response. Each of IR spectrum 602 and reduced IR spectrum 604 has x-axis 608 of frequency measured in THz. IR spectrum 602 may be one of set of IR spectra 208 of FIG. 2.

In some illustrative examples, a rank revealing matrix factorization applied to a matrix formed by set of IR spectra 300 of FIG. 3 is applied to IR spectrum 602 forms reduced IR spectrum 604. In some illustrative examples, the rank revealing matrix factorization is a "rank revealing" QR or LU factorization method. Reduced IR spectrum 604 presents a basis vector for compound D. In the depicted illustrative example, values in the basis vector for compound D are values in reduced IR spectrum 504.

In other non-depicted examples, values in the basis vectors for compound D are a mixed spectrum basis. In some of these non-depicted illustrative examples, a truncated SVD or rank-revealing URV/ULV is used.

As can be seen from view 600, applying the rank revealing matrix factorization creates reduced IR spectrum 604 with frequencies 610. Frequencies 610 has seven points. As can be seen in reduced IR spectrum 604, compound D has high value 612 at frequency 614, high value 616 at frequency 618, and low values at the remaining frequencies of frequencies 610. The values for each of frequencies 610 together distinguish compound D from each of compound A, compound B, compound C, compound E, compound F, and compound G. In some illustrative examples, high value 612 and high value 616 along with the low values at the remaining frequencies distinguish compound D from other possible compounds not included in identified compounds.

FIGS. 4-6 depict respective IR spectra and reduced IR spectra for identified compounds of a set of identified compounds in FIG. 3. A transformation created using a rank revealing matrix factorization applied to a matrix formed by set of IR spectra 300 of FIG. 3 is applied to an IR spectrum for a material sample to detect the compounds of the set of identified compounds. FIGS. 7 and 8 depict an IR spectrum for a material sample and a reduced IR spectrum for the material sample created by applying the transformation created using set of IR spectra 300 of FIG. 3.

Turning now to FIG. 7, an illustration of an IR spectrum for a material sample is depicted in accordance with an illustrative embodiment. IR spectrum 700 is an implementation of IR spectrum 110 of FIG. 1. IR spectrum 700 is an implementation of IR spectrum 206 of FIG. 2.

IR spectrum 700 is a measured IR spectrum of a material sample from an IR spectrometer. IR spectrum 700 has y-axis 702 and x-axis 704. X-axis 704 is measured in Frequency (THz). IR spectrum 700 has several peaks.

Turning now to FIG. 8, an illustration of a reduced IR spectrum for a material sample is depicted in accordance with an illustrative embodiment. Reduced IR spectrum 800 is an implementation of reduced IR spectrum 130. Reduced IR spectrum 800 is an implementation of a reduced IR spectrum created by operation 220 of FIG. 2.

A transformation created based on set of IR spectra 300 of FIG. 3 is applied to IR spectrum 700 to form a transformed IR spectrum: reduced IR spectrum 800. As depicted, high value 802 is visible at frequency 804. As depicted, high value 802 at frequency 804 and the low values at the remaining frequencies of frequencies 806 are indicative of compound spectrum 314 for compound E and compound spectrum 308 for compound B.

After creating reduced IR spectrum 800, a compressed sensing decomposition is performed on reduced IR spectrum 800. The compressed sensing decomposition determines even very small values for each of frequencies 806. In some illustrative examples, the output of a compressed sensing decomposition will provide the identity of the compound represented by values of frequencies 806. In some illustrative examples, the output of a compressed sensing decomposition will be unsuccessful, providing negative values. When the decomposition is unsuccessful, additional analysis is performed on IR spectrum 700.

Reduced IR spectrum 800 is created using a transformation matrix. As depicted, reduced IR spectrum 800 is created using a "rank revealing" QR or LU factorization method. The illustrative examples are not limited to QR or LU factorization methods. In other non-depicted illustrative examples, a vector with a mixed spectrum basis is created. In these non-depicted illustrative examples, a truncated SVD or rank-revealing URV/ULV is used.

The different components shown in FIGS. 2-8 may be combined with components in FIG. 1, used with components in FIG. 1, or a combination of the two. Additionally, some of the components in FIGS. 2-8 may be illustrative examples of how components shown in block form in FIG. 1 may be implemented as physical structures.

Figure 9:
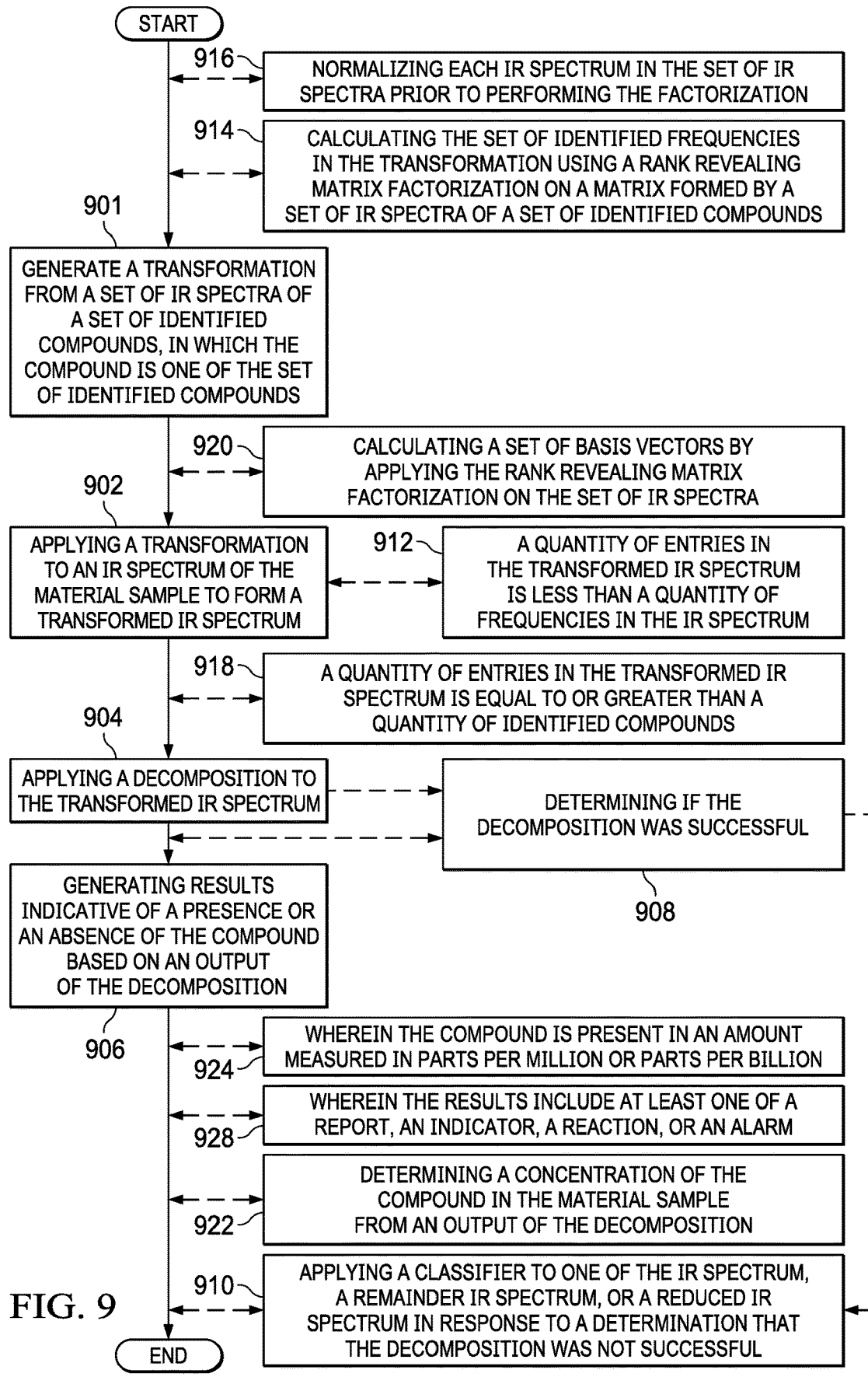
FIG. 9 is an illustration of a flowchart of a method for detecting a compound in a material sample in accordance with an illustrative example.

Turning now to FIG. 9, an illustration of a flowchart of a method for detecting a compound in a material sample is depicted in accordance with an illustrative embodiment. Method 900 may be implemented in detection environment 102 of FIG. 1 using chemical analyzer 100. Method 900 may implement steps of at least one of process 202 or process 204 of FIG. 2.

Method 900 generates a transformation from a set of IR spectra of a set of identified compounds, in which the compound is one of the set of identified compounds (operation 901). Method 900 applies a transformation to an IR spectrum of the material sample to form a transformed IR spectrum (operation 902). Method 900 applies a decomposition to the transformed IR spectrum (operation 904). Method 900 generates results indicative of a presence or an absence of the compound based on an output of the decomposition (operation 906). Afterwards, method 900 terminates.

In some illustrative examples, method 900 determines if the decomposition was successful (operation 908). In some illustrative examples, operation 906 is performed in response to determining that the decomposition was successful. In some illustrative examples, method 900 applies a classifier to the IR spectrum in response to a determination that the decomposition was not successful (operation 910).

In some illustrative examples, a quantity of entries in the transformed IR spectrum is less than a quantity of frequencies in the IR spectrum (operation 912). In some illustrative examples, applying the dimensional reduction may be described as removing frequencies from the IR spectrum that are not present in the set of identified frequencies.

The set of identified frequencies are calculated using a set of IR spectra of a set of identified compounds. In some illustrative examples, the sets of identified frequencies in the transformation are calculated using rank revealing matrix factorization on a matrix formed by a set of IR spectra of a set of identified compounds (operation 914). In some illustrative examples, the set of identified frequencies in the dimensional reduction are calculated using QR factorization with column pivoting from a matrix formed by a set of IR spectra of a set of identified compounds. In some illustrative examples, method 900 further comprises normalizing each IR spectrum in the set of IR spectra prior to performing the factorization (operation 916).

In method 900, a quantity of entries in the transformed IR spectrum is equal to or greater than a quantity of identified compounds (operation 918). In some illustrative examples, method 900 calculates a set of basis vectors by applying the rank revealing matrix factorization on the set of IR spectra (operation 920). In some illustrative examples, the set of basis vectors is a reduced spectra for each of the identified compounds.

In some illustrative examples, method 900 determines a concentration of the compound in the material sample from an output of the decomposition (operation 922). When a concentration of the compound is determined, the concentration may be reproduced in the results generated in operation 906.

Method 900 is capable of identifying the presence of a compound not detectable by conventional means. In some illustrative examples of method 900, the compound is present in an amount measured in parts per million or parts per billion (operation 924). In some illustrative examples, the results include at least one of a report, an indicator, a reaction, or an alarm (operation 928).

Figure 10:
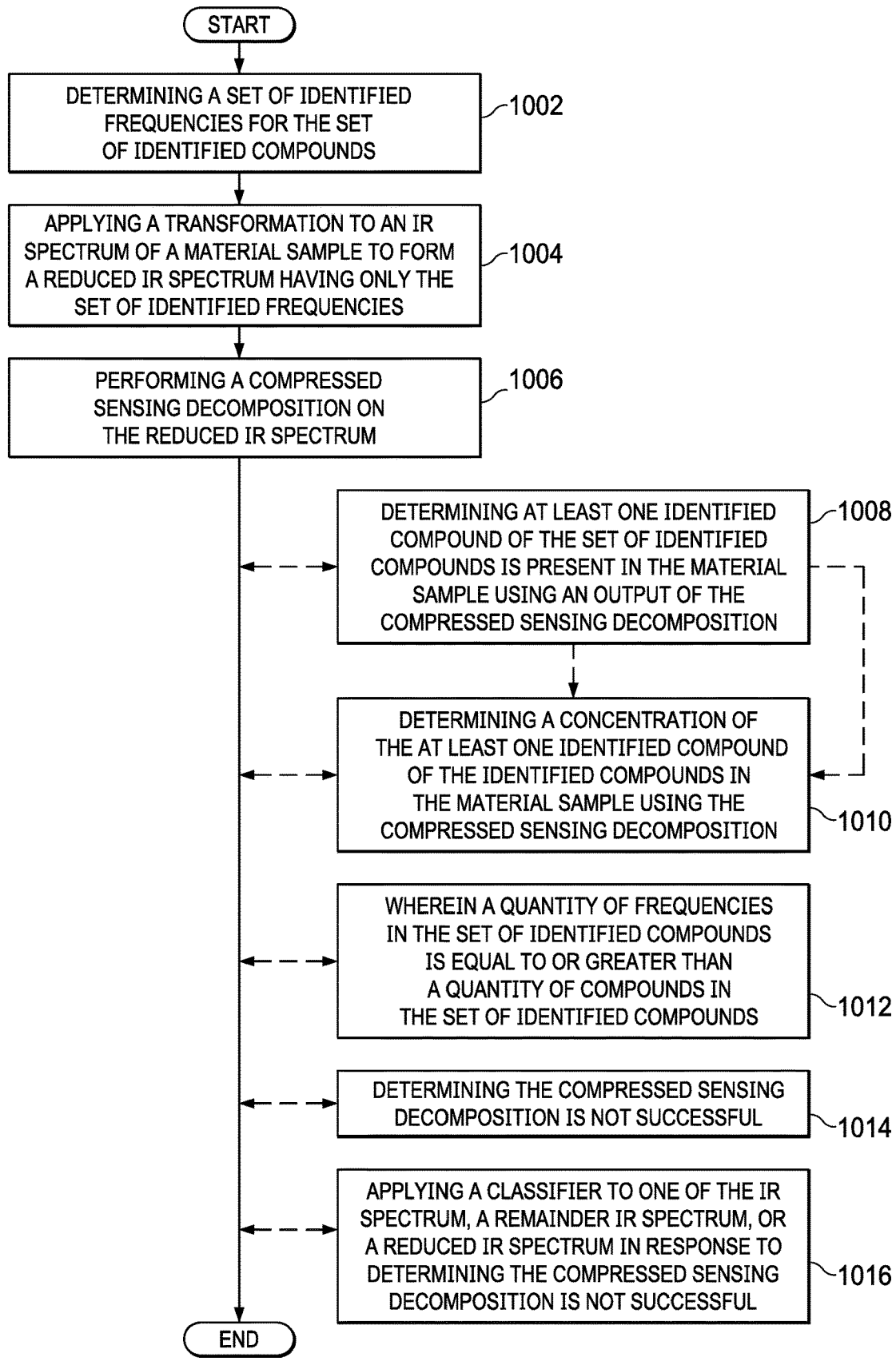
FIG. 10 is an illustration of a flowchart of a method for monitoring samples for presence of a set of identified compounds in accordance with an illustrative example.

Turning now to FIG. 10, an illustration of a flowchart of a method for monitoring samples for presence of a set of identified compounds is depicted in accordance with an illustrative embodiment. Method 1000 may be implemented in detection environment 102 of FIG. 1 using chemical analyzer 100. Method 1000 may implement steps of at least one of process 202 or process 204 of FIG. 2.

Method 1000 determines a set of identified frequencies for the set of identified compounds (operation 1002). Method 1000 applies a transformation to an IR spectrum of a material sample to form a reduced IR spectrum having only the set of identified frequencies (operation 1004). Method 1000 performs a compressed sensing decomposition on the reduced IR spectrum (operation 1006). Afterwards, method 1000 terminates.

In some illustrative examples, method 1000 further comprises determining at least one identified compound of the set of identified compounds is present in the material sample using an output of the compressed sensing decomposition (operation 1008). The output of the compressed sensing decomposition provides a numerical value for each identified compound of the set of identified compounds. An identified compound is identified to be present when the numerical value of the output of the compressed sensing decomposition assigned to that identified compound reaches a threshold value.

In some illustrative examples, method 1000 further comprises determining a concentration of the at least one identified compound of the set of identified compounds in the material sample using the compressed sensing decomposition (operation 1010). The numerical values in the output of the compressed sensing decomposition are indicative of the concentrations of each identified compound. In some illustrative examples, a quantity of frequencies in the set of identified frequencies is equal to or greater than a quantity of compounds in the set of identified compounds (operation 1012). The quantity of frequencies is sufficient to distinguish each of the compounds in the set of identified compounds from each other.

In some illustrative examples, method 1000 optionally determines the compressed sensing decomposition is not successful (operation 1014). The compressed sensing decomposition is not successful when a negative value is returned in the output of the compressed sensing decomposition. In some illustrative examples, method 1000 applies a classifier to one of the IR spectrum, a remainder IR spectrum, or a reduced IR spectrum in response to determining the compressed sensing decomposition is not successful (operation 1016).

Figure 11:
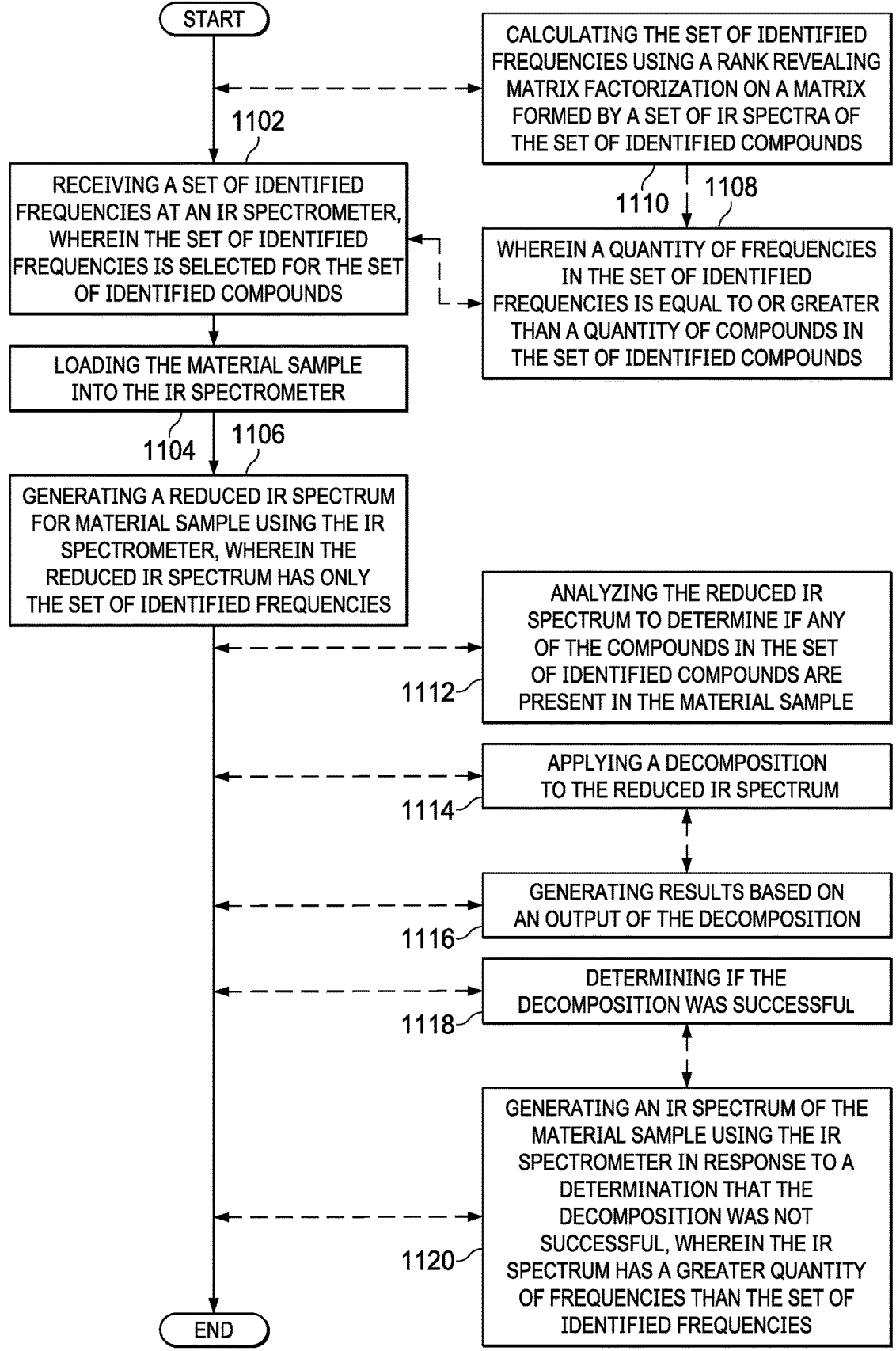
FIG. 11 is an illustration of a flowchart of a method for monitoring for a set of identified compounds in a material sample in accordance with an illustrative example.

Turning now to FIG. 11, an illustration of a flowchart of a method for monitoring for a set of identified compounds in a material sample is depicted in accordance with an illustrative embodiment. Method 1100 may be implemented in detection environment 102 of FIG. 1 using IR spectrometer 128. Method 1100 may implement steps of at least one of process 202 or process 204 of FIG. 2.

Method 1100 receives a set of identified frequencies at an IR spectrometer, wherein the set of identified frequencies is selected for the set of identified compounds (operation 1102). Method 1100 loads the material sample into the IR spectrometer (operation 1104). Method 1100 generates a reduced IR spectrum for the material sample using the IR spectrometer, wherein the reduced IR spectrum has only the set of identified frequencies (operation 1106). Afterwards, method 1100 terminates.

In some illustrative examples, a quantity of frequencies in the set of identified frequencies is equal to or greater than a quantity of compounds in the set of identified compounds (operation 1108). In some illustrative examples, method 1100 further comprises calculating the set of identified frequencies using a rank revealing matrix factorization on a matrix formed by a set of IR spectra of the set of identified compounds (operation 1110). In some illustrative examples, method 1100 further comprises calculating the set of identified frequencies using a rank revealing matrix factorization on a matrix formed by a set of IR spectra of the set of identified compounds.

In some illustrative examples, method 1100 further comprises analyzing the reduced IR spectrum for the material sample to determine if any of the compounds in the set of identified compounds are present in the material sample (operation 1112). In some illustrative examples, method 1100 applies a decomposition to the reduced IR spectrum (operation 1114). In some illustrative examples, method 1100 generates results based on an output of the decomposition (operation 1116).

In some illustrative examples, method 1100 determines if the decomposition was successful (operation 1118). In some illustrative examples, method 1100 generates an IR spectrum of the material sample using the IR spectrometer in response to a determination that the decomposition was not successful, wherein the IR spectrum has a greater quantity of frequencies than the set of identified frequencies (operation 1120).

Figure 12:
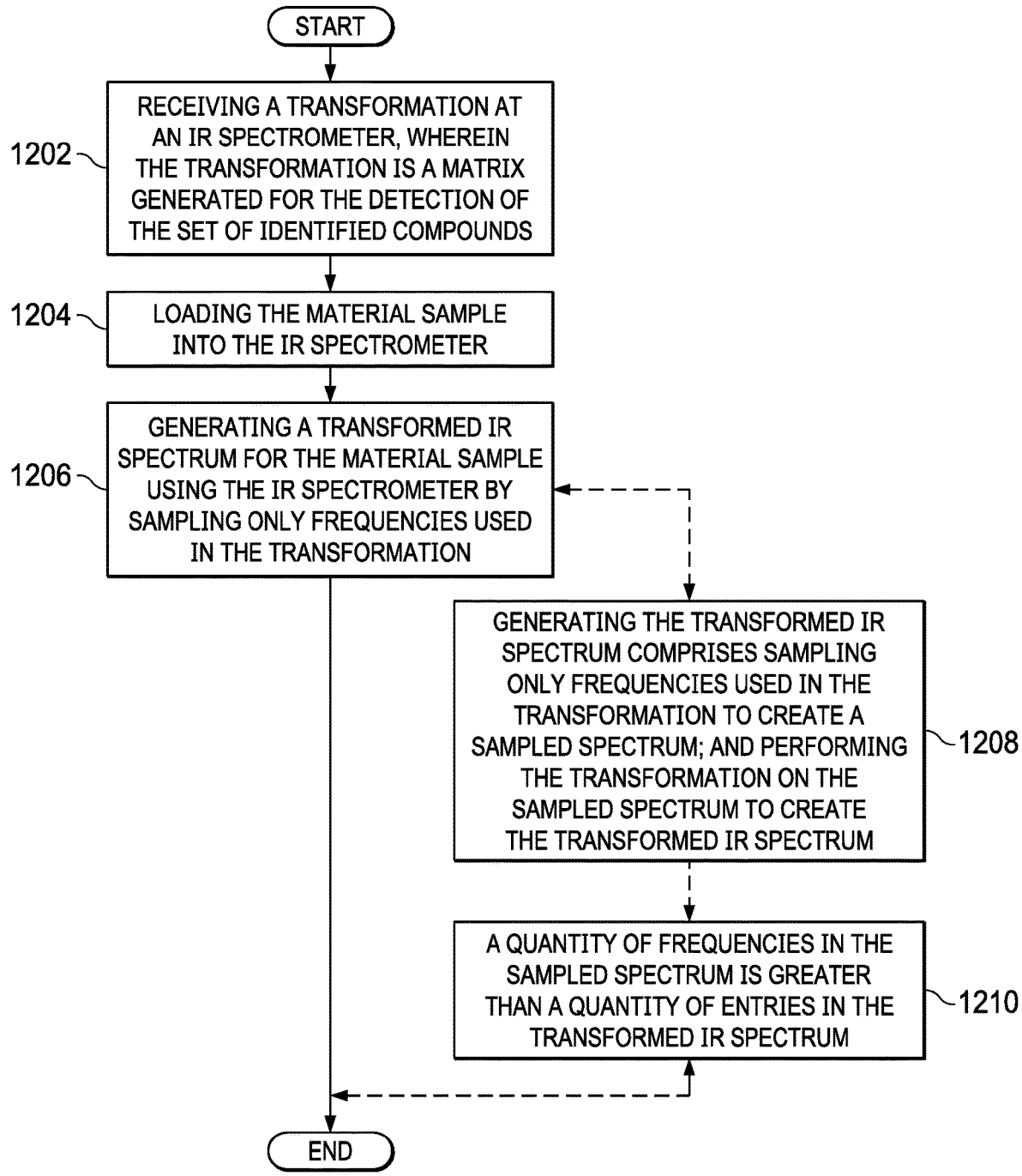
FIG. 12 is an illustration of a flowchart of a method for monitoring for a set of identified compounds in a material sample in accordance with an illustrative example.

Turning now to FIG. 12, an illustration of a flowchart of a method for monitoring for a set of identified compounds in a material sample is depicted in accordance with an illustrative embodiment. Method 1200 may be implemented in detection environment 102 of FIG. 1 using IR spectrometer 128. Method 1200 may implement steps of at least one of process 202 or process 204 of FIG. 2.

Method 1200 receives a transformation at an IR spectrometer, wherein the transformation is a matrix generated for the detection of the set of identified compounds (operation 1202). Method 1200 loads the material sample into the IR spectrometer (operation 1204). Method 1200 generates a transformed IR spectrum for the material sample using the IR spectrometer by sampling only frequencies used in the transformation (operation 1206). Afterwards, method 1200 terminates.

In some illustrative examples, generating the transformed IR spectrum comprises sampling only frequencies used in the transformation to create a sampled spectrum; and performing the transformation on the sampled spectrum to create the transformed IR spectrum (operation 1208). In some illustrative examples, a quantity of frequencies in the sampled spectrum is greater than a quantity of entries in the transformed IR spectrum (operation 1210).

The flowcharts and block diagrams in the different depicted embodiments illustrate the architecture, functionality, and operation of some possible implementations of apparatus and methods in an illustrative embodiment. In this regard, each block in the flowcharts or block diagrams may represent a module, a segment, a function, and/or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added, in addition to the illustrated blocks, in a flowchart or block diagram. Some blocks may be optional. For example, in method 900, operations 908 through 928 may be optional. As another example, in method 1000, operations 1008 through 1016 may be optional. As yet another example, in method 1100, operations 1108 through 1120 may be optional. As a further example, in method 1200, operations 1208 and 1210 may be optional.

Figure 13:
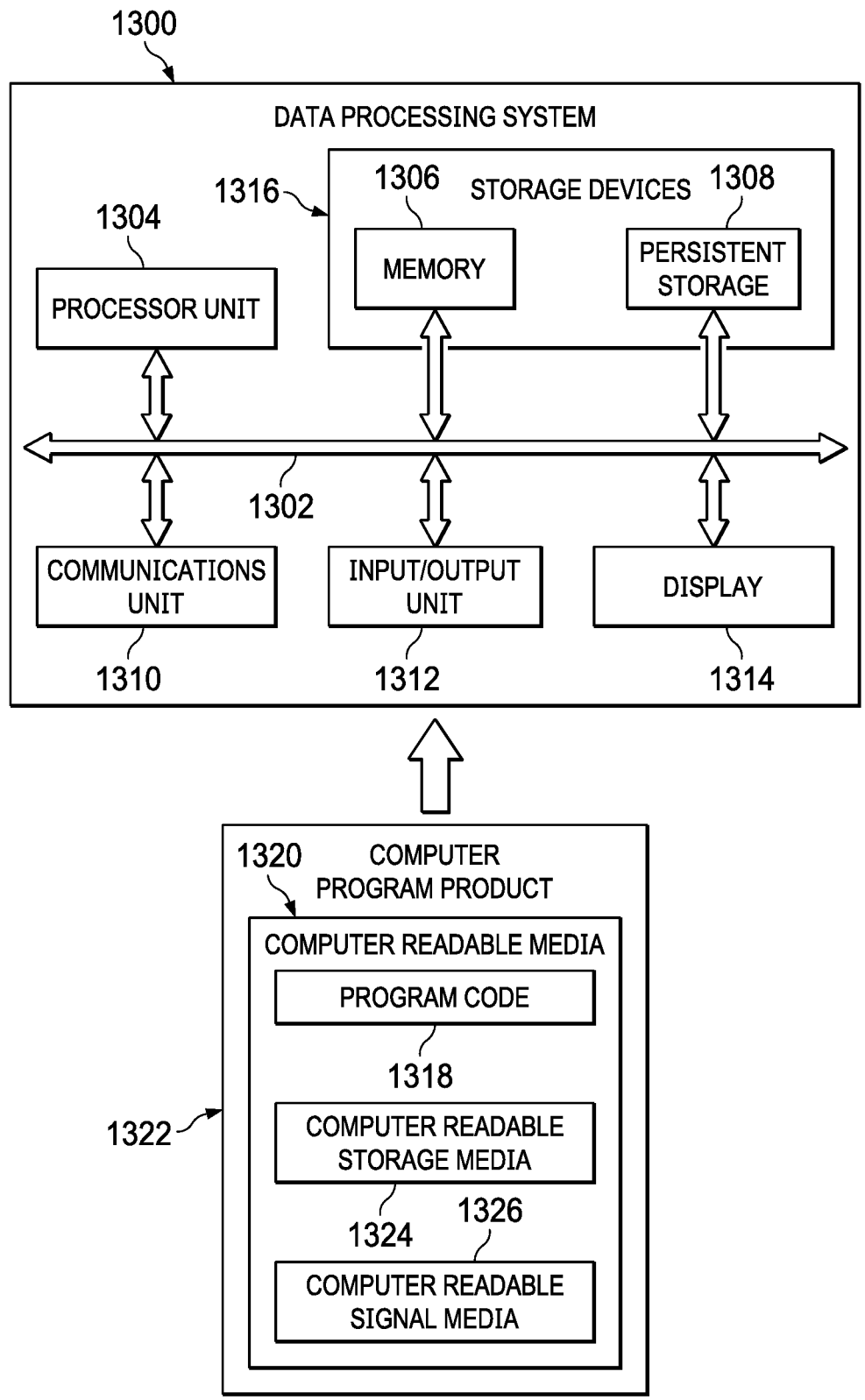
FIG. 13 is an illustration of a data processing system in a form of a block diagram in accordance with an illustrative embodiment.

Turning now to FIG. 13, an illustration of a data processing system in a form of a block diagram is depicted in accordance with an illustrative embodiment. Data processing system 1300 may be used to implement at least one of computer system 148 of FIG. 1.

In this illustrative example, data processing system 1300 includes communications fabric 1302. Communications fabric 1302 provides communications between processor unit 1304, memory 1306, persistent storage 1308, communications unit 1310, input/output (I/O) unit 1312, and display 1314. Memory 1306, persistent storage 1308, communications unit 1310, input/output (I/O) unit 1312, and display 1314 are examples of resources accessible by processor unit 1304 via communications fabric 1302.

Processor unit 1304 serves to run instructions for software that may be loaded into memory 1306. Processor unit 1304 may be a number of processors, a multi-processor core, or some other type of processor, depending on the particular implementation. Further, processor unit 1304 may be implemented using a number of heterogeneous processor systems in which a main processor is present with secondary processors on a single chip. As another illustrative example, processor unit 1304 may be a symmetric multi-processor system containing multiple processors of the same type.

Memory 1306 and persistent storage 1308 are examples of storage devices 1316. A storage device is any piece of hardware that is capable of storing information, such as, for example, without limitation, data, program code in functional form, and other suitable information either on a temporary basis or a permanent basis. Storage devices 1316 also may be referred to as computer readable storage devices in these examples. Memory 1306, in these examples, may be, for example, a random access memory or any other suitable volatile or non-volatile storage device. Persistent storage 1308 may take various forms, depending on the particular implementation.

For example, persistent storage 1308 may contain one or more components or devices. For example, persistent storage 1308 may be a hard drive, a flash memory, a rewritable optical disk, a rewritable magnetic tape, or some combination of the above. The media used by persistent storage 1308 also may be removable. For example, a removable hard drive may be used for persistent storage 1308.

Communications unit 1310, in these examples, provides for communications with other data processing systems or devices. In these examples, communications unit 1310 is a network interface card. Communications unit 1310 may provide communications through the use of either or both physical and wireless communications links.

Input/output (I/O) unit 1312 allows for input and output of data with other devices that may be connected to data processing system 1300. For example, input/output (I/O) unit 1312 may provide a connection for user input through a keyboard, a mouse, and/or some other suitable input device. Further, input/output (I/O) unit 1312 may send output to a printer. Display 1314 provides a mechanism to display information to a user.

Instructions for the operating system, applications, and/or programs may be located in storage devices 1316, which are in communication with processor unit 1304 through communications fabric 1302. In these illustrative examples, the instructions are in a functional form on persistent storage 1308. These instructions may be loaded into memory 1306 for execution by processor unit 1304. The processes of the different embodiments may be performed by processor unit 1304 using computer-implemented instructions, which may be located in a memory, such as memory 1306.

These instructions are referred to as program instructions, program code, computer usable program code, or computer readable program code that may be read and executed by a processor in processor unit 1304. The program code in the different embodiments may be embodied on different physical or computer readable storage media, such as memory 1306 or persistent storage 1308.

Program code 1318 is located in a functional form on computer readable media 1320 that is selectively removable and may be loaded onto or transferred to data processing system 1300 for execution by processor unit 1304. Program code 1318 and computer readable media 1320 form computer program product 1322 in these examples. In one example, computer readable media 1320 may be computer readable storage media 1324 or computer readable signal media 1326.

In one illustrative example, computer program product 1322 is a computer program product for detecting a compound in a material sample. Computer program product 1322 may be present within detection environment 102 for detecting compound 104 in material sample 106. In these illustrative examples, computer program product 1322 comprises computer-readable storage medium 1324 having computer-readable program code 1318 embodied therewith, the computer-readable program code 1318 executable by one or more computer processors, such as processor unit 1304, to apply a dimensional reduction to an IR spectrum of the material sample to form a reduced IR spectrum; apply a decomposition to the reduced IR spectrum; and generate results based on an output of the decomposition.

Computer readable storage media 1324 may include, for example, an optical or magnetic disk that is inserted or placed into a drive or other device that is part of persistent storage 1308 for transfer onto a storage device, such as a hard drive, that is part of persistent storage 1308. Computer readable storage media 1324 also may take the form of a persistent storage, such as a hard drive, a thumb drive, or a flash memory, that is connected to data processing system 1300. In some instances, computer readable storage media 1324 may not be removable from data processing system 1300.

In these examples, computer readable storage media 1324 is a physical or tangible storage device used to store program code 1318 rather than a medium that propagates or transmits program code 1318. Computer readable storage media 1324 is also referred to as a computer readable tangible storage device or a computer readable physical storage device. In other words, computer readable storage media 1324 is a media that can be touched by a person.

Alternatively, program code 1318 may be transferred to data processing system 1300 using computer readable signal media 1326. Computer readable signal media 1326 may be, for example, a propagated data signal containing program code 1318. For example, computer readable signal media 1326 may be an electromagnetic signal, an optical signal, and/or any other suitable type of signal. These signals may be transmitted over communications links, such as wireless communications links, optical fiber cable, coaxial cable, a wire, and/or any other suitable type of communications link. In other words, the communications link and/or the connection may be physical or wireless in the illustrative examples.

In some illustrative embodiments, program code 1318 may be downloaded over a network to persistent storage 1308 from another device or data processing system through computer readable signal media 1326 for use within data processing system 1300. For instance, program code stored in a computer readable storage medium in a server data processing system may be downloaded over a network from the server to data processing system 1300. The data processing system providing program code 1318 may be a server computer, a client computer, or some other device capable of storing and transmitting program code 1318.

The different components illustrated for data processing system 1300 are not meant to provide architectural limitations to the manner in which different embodiments may be implemented. The different illustrative embodiments may be implemented in a data processing system including components in addition to and/or in place of those illustrated for data processing system 1300. Other components shown in FIG. 13 can be varied from the illustrative examples shown. The different embodiments may be implemented using any hardware device or system capable of running program code. As one example, data processing system 1300 may include organic components integrated with inorganic components and/or may be comprised entirely of organic components excluding a human being. For example, a storage device may be comprised of an organic semiconductor.

In another illustrative example, processor unit 1304 may take the form of a hardware unit that has circuits that are manufactured or configured for a particular use. This type of hardware may perform operations without needing program code to be loaded into a memory from a storage device to be configured to perform the operations.

For example, when processor unit 1304 takes the form of a hardware unit, processor unit 1304 may be a circuit system, an application specific integrated circuit (ASIC), a programmable logic device, or some other suitable type of hardware configured to perform a number of operations. With a programmable logic device, the device is configured to perform the number of operations. The device may be reconfigured at a later time or may be permanently configured to perform the number of operations. Examples of programmable logic devices include, for example, a programmable logic array, a programmable array logic, a field programmable logic array, a field programmable gate array, and other suitable hardware devices. With this type of implementation, program code 1318 may be omitted, because the processes for the different embodiments are implemented in a hardware unit.

In still another illustrative example, processor unit 1304 may be implemented using a combination of processors found in computers and hardware units. Processor unit 1304 may have a number of hardware units and a number of processors that are configured to run program code 1318. With this depicted example, some of the processes may be implemented in the number of hardware units, while other processes may be implemented in the number of processors.

In another example, a bus system may be used to implement communications fabric 1302 and may be comprised of one or more buses, such as a system bus or an input/output bus. Of course, the bus system may be implemented using any suitable type of architecture that provides for a transfer of data between different components or devices attached to the bus system.

Additionally, communications unit 1310 may include a number of devices that transmit data, receive data, or both transmit and receive data. Communications unit 1310 may be, for example, a modem or a network adapter, two network adapters, or some combination thereof. Further, a memory may be, for example, memory 1306, or a cache, such as that found in an interface and memory controller hub that may be present in communications fabric 1302.

The illustrative examples provide extraction of a feature basis (rather than the original full spectrum) that both compresses the spectra and will be used for the decomposition. Extracting a feature basis provides a way to break down a spectrum into smaller signatures (for example, separating out the functional groups in an organic compound) that can then be used to identify new compounds in combination. Extracting a feature basis also improves the decomposition step performance because the extraction identifies the truly differentiating features of the spectra. The extraction of a feature basis also serves as a compression mechanism.

Compression helps reduce the computational needs during the decomposition step and also reduces data transmission needs. Reducing the data transmission needs are beneficial for scenarios like when the IR sensors on a moving platform.

In some illustrative examples, a frequency distribution function is used to provide another compression mechanism. When used, a frequency distribution function also provides a mechanism to handle sensor noise or variation. For instance, there is expected to be some amount of variance for a given chemical signature. If, for example, a thousand measurements of the same material are taken, there will be some variability. Using a frequency spacing that is tailored to that variance would be a better representation of the chemical signature.

The illustrative examples utilize a compressed sensing decomposition on the reduced IR spectrum represented by the transformed IR spectrum. In some illustrative examples, the results of the decomposition step are used with a machine learning step to provide clues on potential new substances.

If any of the components of the reduced IR spectrum in the output of the compressed sensing decomposition are negative, additional analysis of the spectrum of the material sample is performed. In some illustrative examples, the analysis is performed on the full spectrum of the material sample. In other illustrative examples, the analysis is performed on a reduced IR spectrum. The analysis is performed on one of the full spectrum or the reduced IR spectrum to determine which of the known compounds is the closest match using machine learning. In some illustrative examples, to perform the machine learning, the threshold for determination of a compound may be set lower during this analysis. The machine learning returns the closest match compound and the difference in spectra between the closest compound and the remainder spectrum.

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method of detecting a compound in a material sample, the method comprising:
   generating a transformation from a set of IR spectra of a set of identified chemical compounds, in which the compound is one of the set of identified chemical compounds;
   applying the transformation to an IR spectrum of the material sample to form a transformed IR spectrum;
   applying a decomposition to the transformed IR spectrum, wherein the decomposition is different than the transformation; and
   generating results indicative of a presence or an absence of the compound based on an output of the decomposition.

2. The method of claim 1 further comprising:
   determining if the decomposition was successful; and
   applying a classifier to one of the IR spectrum, a remainder IR spectrum, or a reduced IR spectrum in response to a determination that the decomposition was not successful.

3. The method of claim 1, wherein a quantity of entries in the transformed IR spectrum is less than a quantity of frequencies in the IR spectrum.

4. The method of claim 1, wherein a quantity of entries in the transformed IR spectrum is equal to or greater than a quantity of compounds in the set of identified chemical compounds.

5. The method of claim 4 further comprising:
   calculating a set of identified frequencies in the transformation using a rank revealing matrix factorization on a matrix formed by a set of IR spectra of the set of identified chemical compounds.

6. The method of claim 5 further comprising:
   calculating a set of basis vectors by applying the rank revealing matrix factorization on the set of IR spectra.

7. The method of claim 5 further comprising:
   normalizing each IR spectrum in the set of IR spectra prior to performing the rank revealing matrix factorization.

8. The method of claim 1 further comprising:
   determining a concentration of the compound in the material sample from an output of the decomposition.

9. The method of claim 1, wherein the compound is present in an amount measured in parts per million or parts per billion.

10. The method of claim 1, wherein the results include at least one of a report, an indicator, a reaction, or an alarm.

11. A method of monitoring samples for presence of a set of identified compounds, the method comprising:
    determining a set of identified frequencies for the set of identified compounds;
    applying a transformation to an IR spectrum of a material sample to form a reduced IR spectrum having only the set of identified frequencies; and
    performing a compressed sensing decomposition on the reduced IR spectrum, wherein the compressed sensing decomposition is different than the transformation.

12. The method of claim 11 further comprising:
    determining at least one identified compound of the set of identified compounds is present in the material sample using an output of the compressed sensing decomposition.

13. The method of claim 12 further comprising:
determining a concentration of the at least one identified compound of the set of identified compounds in the material sample using the compressed sensing decomposition.

14. The method of claim 11, wherein a quantity of frequencies in the set of identified frequencies is equal to or greater than a quantity of compounds in the set of identified compounds.

15. The method of claim 11 further comprising:
determining the compressed sensing decomposition is not successful; and
applying a classifier to one of the IR spectrum, a remainder IR spectrum, or a reduced IR spectrum in response to determining the compressed sensing decomposition is not successful.

16. An apparatus for monitoring for a set of identified compounds, the apparatus comprising:
a chemical analyzer configured to:
generate a transformation from a set of IR spectra of a set of identified compounds;
apply the transformation to an IR spectrum of a material sample to form a transformed IR spectrum;
apply a decomposition to the transformed IR spectrum, wherein the decomposition is different than the transformation; and
generate results indicative of a presence or an absence of the set of identified compounds based on an output of the decomposition.

17. The apparatus of claim 16, the apparatus further comprising:
an IR spectrometer configured to generate the IR spectrum of the material sample.

18. The apparatus of claim 16, the apparatus further comprising:
a classifier configured to determine a type of chemical within the material sample.

19. A computer program product for detecting a compound in a material sample, the computer program product comprising:
a non-transitory, computer-readable storage medium including instructions configured to cause one or more computer processors to:
generate a transformation from a set of IR spectra of a set of identified compounds, in which the compound is one of the set of identified compounds;
apply a transformation to an IR spectrum of the material sample to form a transformed IR spectrum;
apply a decomposition to the transformed IR spectrum, wherein the decomposition is different than the transformation; and
generate results indicative of a presence or an absence of the compound based on an output of the decomposition.

20. The method of claim 1, wherein the decomposition comprises a spectral decomposition of the transformed IR spectrum of the material sample, and the method further comprises:
applying a linear least squares fit to the output of the decomposition prior to generating the results.

21. The method of claim 20, wherein the output of the decomposition determines a concentration of each identified chemical compound of the set of identified chemical compounds.

* * * * *